United States Patent
Zwirn et al.

(10) Patent No.: US 7,529,398 B2
(45) Date of Patent: May 5, 2009

(54) HIGH RESOLUTION RADIO FREQUENCY MEDICAL IMAGING AND THERAPY SYSTEM

(76) Inventors: Gil Zwirn, 29 A.D. Gordon St., Petah Tikva 49280 (IL); Moshe Margalit, 2 Hagaon Eliyahu St., Ramat Gan 52364 (IL)

(*) Notice: Subject to any disclaimer, the term of this patent is extended or adjusted under 35 U.S.C. 154(b) by 0 days.

(21) Appl. No.: 11/997,913

(22) PCT Filed: Aug. 3, 2006

(86) PCT No.: PCT/IL2006/000896

§ 371 (c)(1),
(2), (4) Date: Feb. 5, 2008

(87) PCT Pub. No.: WO2007/017861

PCT Pub. Date: Feb. 15, 2007

(65) Prior Publication Data

US 2008/0228062 A1 Sep. 18, 2008

Related U.S. Application Data

(60) Provisional application No. 60/707,064, filed on Aug. 9, 2005.

(51) Int. Cl.
*G06K 9/00* (2006.01)
(52) U.S. Cl. .................................. 382/131
(58) Field of Classification Search ......... 382/128–131, 382/154, 274, 275; 600/407, 408, 409, 430, 600/547, 2, 10; 324/637, 638, 639
See application file for complete search history.

(56) References Cited

U.S. PATENT DOCUMENTS 6,253,100 B1    6/2001   Zhdanov (Continued)

FOREIGN PATENT DOCUMENTS

WO    WO03003907    1/2003

OTHER PUBLICATIONS

Yariv in Optical Electronics, CBS College Publishing, 1985, Chapter 4, pp. 87-95.

(Continued)

*Primary Examiner*—Sherali Ishrat
(74) *Attorney, Agent, or Firm*—Martin Fleit; Paul D. Bianco; Fleit Gibbons Gutman Bongini & Bianco PL

(57) ABSTRACT

A method for imaging includes directing a plurality of radio frequency (RF) beams (206, 207) toward a target organ from a plurality of angles. The RF beams include one or more first pairs of the RF beams, each first pair including two of the RF beams that impinge on the target organ from opposite directions. RF signals reflected from the target organ are received responsively to the RF beams, the RF signals including one or more second pairs of the RF signals engendered respectively by the one or more first pairs of the RF beams. Local tissue parameters at multiple points in the target organ are extracted by jointly processing the RF signals in each of the second pairs. Images of the target organ are produced using the extracted local tissue parameters. Other embodiments described herein include methods for passive imaging, motion vector analysis, ablation, local heating and application of electromagnetic pressure.

25 Claims, 11 Drawing Sheets

U.S. PATENT DOCUMENTS

| | | |
|---|---|---|
| 6,448,788 B1 | 9/2002 | Meaney et al. |
| 6,490,471 B2 | 12/2002 | Svenson et al. |
| 7,454,242 B2 * | 11/2008 | Fear et al. .................. 600/430 |
| 2003/0088180 A1 * | 5/2003 | Van Veen et al. ............ 600/430 |

OTHER PUBLICATIONS

Jackson in "Classical Electrodynamics," John Wiley & Sons Inc., New York, 1999, pp. 295-316.

Gabriel et al., in "The Dielectric Properties of Biological Tissues: I. Literature Survey," Physics in Medicine and Biology, vol. 41, 1996, pp. 2231-2249.

Borison et al., in "Super-Resolution Methods for Wideband Radar," The Massachusetts Institute of Technology Lincoln Laboratory Journal, (5:3), 1992, pp. 441-461.

Kandel et al., in "Principles of Neural Science," McGraw-Hill, New York, 2000, pp. 19-35.

Instruction #6055.11 of the U.S. Department of Defense (DoD) entitled "Protection of DoD Personnel from Exposure to Radiofrequency Radiation and Military Exempt Lasers," Febru.

* cited by examiner

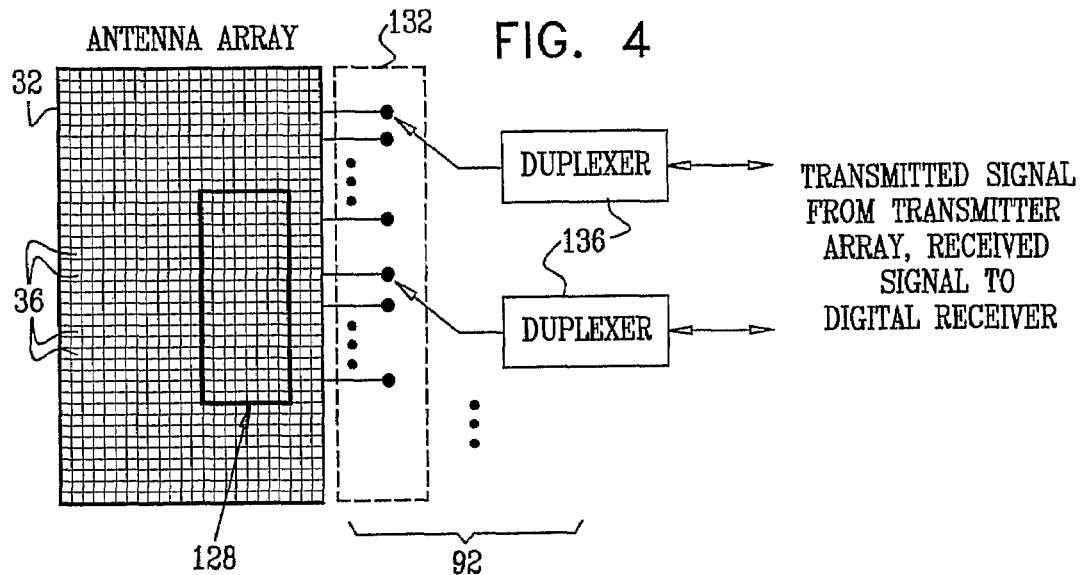
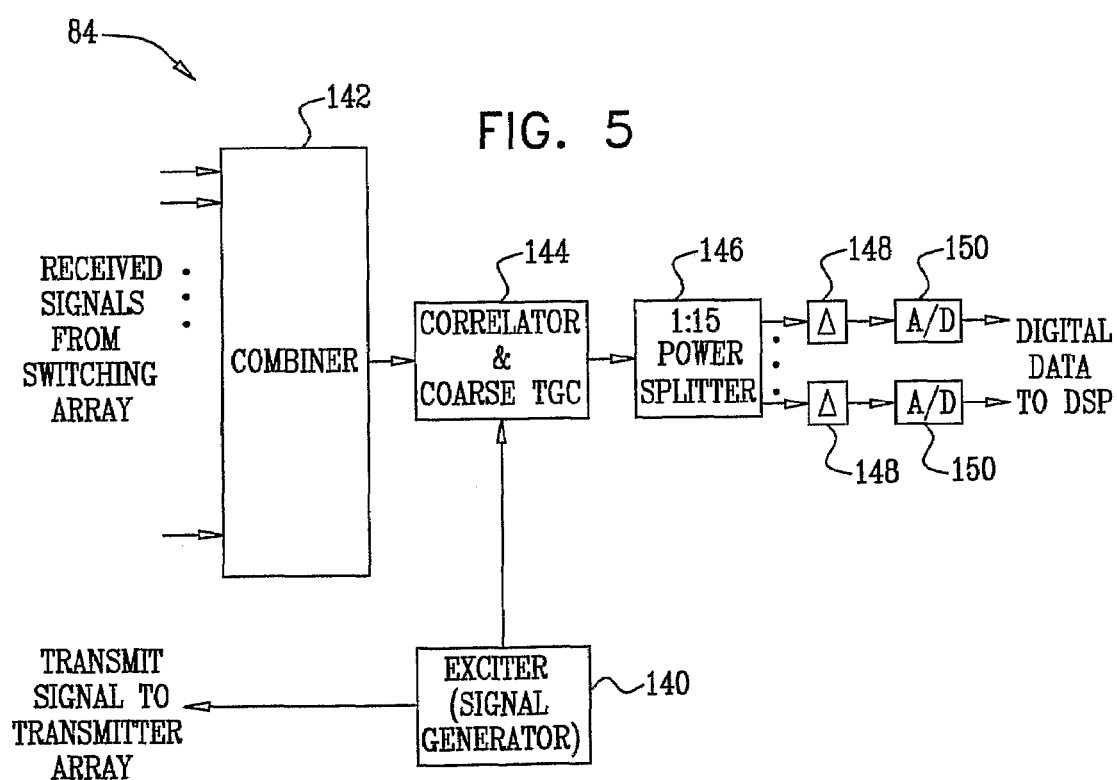

HIGH RESOLUTION RADIO FREQUENCY MEDICAL IMAGING AND THERAPY SYSTEM

CROSS-REFERENCE TO RELATED APPLICATIONS

This application claims the benefit of U.S. Provisional Patent Application 60/707,064, filed Aug. 9, 2005, which is incorporated herein by reference.

FIELD OF THE INVENTION

The present invention relates generally to medical imaging and therapy systems, and particularly to methods and systems for high resolution radio frequency (RF) imaging and therapy.

BACKGROUND OF THE INVENTION

Medical imaging methods and systems use a variety of imaging modalities. Each modality can be characterized by its typical spatial and temporal resolution. For example, the following table shows typically achievable spatial and temporal resolution values of several known imaging modalities:

| Modality | Spatial resolution (per axis) [mm] | Temporal resolution (three-dimensional frame refresh rate) [Hz] |
| --- | --- | --- |
| Ultrasound | 1 | 20-30 |
| Single positron emission computerized tomography (SPECT) | 5 | 10 |
| Positron emission tomography (PET) | 3 | 10 |
| Computerized tomography (CT) | 0.5-1 | 10 |
| Magnetic resonance imaging (MRI) | 0.5-1 | 10 |

Some methods and systems use radio frequency (RF) based imaging. For example, U.S. Pat. No. 6,490,471, whose disclosure is incorporated herein by reference, describes a single-frequency three-dimensional (3-D) microwave tomographic device capable of imaging a full scale biological object. The device includes code-division software, which cooperates with a microwave patch system to enable superficial imaging of biological systems. A cluster of antennas and transceivers is used to provide microwave tomography (MWT) and electrical impedance tomography (EIT) integrated in a single 3-D microwave system for examining the biological object from a number of views in real-time.

PCT International Publication WO 03/003907, which is incorporated herein by reference, describes a system for microwave imaging via space-time beam-forming. Microwave signals are transmitted from multiple antenna locations into an individual to be examined. Backscattered microwave signals are received at multiple antenna locations, to provide received signals from the antennas. The received signals are processed in a computer to remove the skin interface reflection component of the signal at each antenna. The corrected signal data is processed by a beam-former. The beam-former is scanned over a plurality of different locations in the individual by changing time shifts, filter weights and time-gating of the beam-former process. The output power may be displayed as a function of scan location, with regions of large output power corresponding to significant microwave scatterers such as malignant lesions.

U.S. Pat. No. 6,448,788, whose disclosure is incorporated herein by reference, describes a method and apparatus for microwave imaging of an inhomogeneous target, in particular of biological tissue. The method compensates for the interactions between active and non-active antennas. Measured electric field data is processed in magnitude and phase form, so that unwrapped phase information may be used directly in the image reconstruction. Initial finite element measurements and calculations are used to determine the perimeter dimensions of the target being examined.

U.S. Pat. No. 6,253,100, whose disclosure is incorporated herein by reference, describes a method for imaging an object, such as a diseased human heart or bone, in a non-transparent medium, such as the human body. The method involves placing an array of transmitters and receivers in operational association with the medium. The transmitters generate a harmonic or pulse primary electromagnetic (EM) field, which propagates through the medium. The primary field interacts with the object to produce a scattered field, which is recorded by the receivers. The scattered EM field components measured by the receivers are applied as an artificial EM field to generate a backscattering EM field. Cross power spectra of the primary and backscattering fields or cross correlation between these fields produce a numerical reconstruction of an EM hologram. The desired properties of the medium, such as conductivity or dielectric permittivity, are then derived from this hologram.

SUMMARY OF THE INVENTION

There is therefore provided, in accordance with an embodiment of the present invention, a method for imaging, including:

directing a plurality of radio frequency (RF) beams toward a target organ from a respective plurality of angles, the plurality of the RF beams including one or more first pairs of the RF beams, each first pair including two of the RF beams that impinge on the target organ from opposite directions;

receiving RF signals reflected from the target organ responsively to the RF beams, the RF signals including one or more second pairs of the RF signals engendered respectively by the one or more first pairs of the RF beams;

extracting local tissue parameters at multiple points in the target organ by jointly processing the RF signals in each of the second pairs; and producing images of the target organ using the extracted local tissue parameters.

In some embodiments, directing the plurality of the RF beams includes forming a respective plurality of effective antennas directed to the target organ from the plurality of the angles by selectively activating subsets of radiating elements selected from an antenna array including a plurality of the radiating elements. In another embodiment, the antenna array includes a cylindrical array surrounding the target organ, and the RF beams are parallel, with an offset no greater than one degree, to a base of the cylinder and point toward a central axis of the cylinder from multiple azimuth angles and heights.

In yet another embodiment, directing the plurality of the RF beams includes mechanically scanning one or more antennas so as to transmit from the plurality of the angles. Additionally or alternatively, directing the plurality of the RF beams includes mechanically scanning the target organ with respect to one or more antennas so as to cause the RF beams generated by the antennas to impinge on the target organ from the plurality of the angles.

In a disclosed embodiment, directing the plurality of the RF beams includes transmitting one or more wideband RF pulses in each of the RF beams. In another embodiment, transmitting the one or more pulses includes transmitting a sequence of two or more wideband RF pulses and phase-encoding the sequence by assigning respective phases to the pulses depending on positions of the pulses in the sequence.

In an embodiment, receiving the RF signals includes sampling the reflected RF signals using multiple analog-to-digital (A/D) converters having incremental time offsets with respect to one another. Receiving the RF signals may include enhancing a range resolution of the reflected RF signals using multiple outputs of the multiple analog-to-digital (A/D) converters.

In another embodiment, receiving the RF signals includes applying a time-dependent gain control (TGC) function to the received RF signals.

In yet another embodiment, the local tissue parameters include at least one parameter selected from a group of parameters consisting of a local attenuation coefficient, a local reflection coefficient, a local time delay and a local tissue dielectric property.

In still another embodiment, receiving the RF signals includes measuring for each of the second pairs first and second reflection intensity profiles indicating intensities of the RF signals in the each of the second pairs as a function of time, and jointly processing the RF signals includes comparing the first and second reflection intensity profiles. Comparing the first and second reflection intensity profiles may include identifying in the first reflection intensity profile first reflection peaks reflected from respective tissue interfaces in a first direction, identifying in the second reflection intensity profile second reflection peaks reflected from the respective tissue interfaces in a second direction opposite to the first direction, and calculating corrected values of the local tissue parameters responsively to differences between the first and second reflection peaks.

In some embodiments, calculating the local tissue parameters includes correcting at least one artifact selected from a group consisting of a local time delay and a local attenuation in the first and second reflection intensity profiles.

In an embodiment, producing the images of the target organ includes reconstructing a three-dimensional (3-D) representation of the local tissue parameters by calculating accumulated contributions of the corrected values of the local tissue parameters of the second pairs at the multiple points in the target organ.

In another embodiment, at least some of the RF beams overlap one another, and reconstructing the 3-D representation includes improving a spatial resolution of the 3-D representation using the overlapping RF beams.

Calculating the accumulated contributions may include calculating, for each beam, iso-time surfaces defining loci of some of the multiple points in the target organ having a particular propagation delay with respect to an antenna directing the beam.

In an embodiment, directing the RF beams, receiving the RF signals and extracting the tissue parameters include continually scanning the target organ using the RF beams, and producing the images of the target organ includes producing a sequence of 3-D images that display a variation of the extracted tissue parameters over time.

In another embodiment, the sequence of the 3-D images has a frame rate greater than fifty 3-D frames per second. In yet another embodiment, the frame rate is greater than or equal to one hundred 3-D frames per second.

In still another embodiment, the method includes tracking a temporal variation of a tissue region by measuring differences among respective locations of the tissue region in the sequence of 3-D images.

In an embodiment, the produced images of the target organ have a spatial resolution better than 2 mm. In another embodiment, the spatial resolution is better than 1 mm.

In yet another embodiment, producing the images of the target organ includes differentiating between first and second different tissue types using the extracted local tissue parameters. Additionally or alternatively, producing the images of the target organ includes identifying a tissue type using the extracted local tissue parameters. Further additionally or alternatively, producing the images of the target organ includes measuring a local conductivity in at least some of the multiple points in the target organ using the extracted local tissue parameters.

In an embodiment, the target organ includes a heart. Additionally or alternatively, at least some of the RF beams penetrate a body containing the target organ to a depth greater than 20 cm in order to image at least some of the multiple points in the target organ. In some embodiments, the depth is greater than 30 cm.

In a disclosed embodiment, directing the RF beams includes configuring a first subset of the RF beams to use a first polarization and a second subset of the RF beams to use a second polarization different from the first polarization, and extracting the local tissue parameters includes calculating first values of the local tissue parameters responsively to the first subset of the beams and second values of the local tissue parameters responsively to the second subset of the beams.

In another embodiment, receiving the RF signals includes filtering the received RF signals to produce first and second partial bandwidth RF signals, and extracting the local tissue parameters includes calculating first values of the local tissue parameters responsively to the first partial bandwidth RF signal and second values of the local tissue parameters responsively to the second partial bandwidth RF signal.

In yet another embodiment, the method includes inserting a contrast agent affecting at least one of the local tissue parameters into the target organ.

In still another embodiment, extracting the local tissue parameters includes estimating tissue motion velocities at the multiple points in the target organ by measuring Doppler spectra of the RF signals in three or more of the RF beams.

In some embodiments, the method includes applying RF ablation to an ablation region in the target organ by focusing an ablating signal on the ablation region using at least some of the RF beams. Focusing the ablating signal on the ablation region may include directing the ablating signal based on the produced images of the target organ. In another embodiment, the method includes locally heating a region of the target organ by focusing a heating RF signal on the region using at least some of the RF beams. In yet another embodiment, the method includes applying an electromagnetic pressure to a region of the target organ by focusing an RF signal on the region using at least some of the RF beams.

There is additionally provided, in accordance with an embodiment of the present invention, a method for imaging, including:

configuring a set of antennas so as to define three or more axes of directional reception of radio frequency (RF) signals from a target organ at respective different angles;

using the set of antennas, passively sensing the RF signals emitted along the three or more axes due to a local electrical activity signal generated in the target organ; and determining a location coordinate of the local electrical activity signal based on the sensed RF signals.

In an embodiment, passively sensing the RF signals includes sampling the RF signals at a sampling rate higher than 1 GHz and integrating the sampled RF signals over a duration greater than or equal to 1 microsecond. In another embodiment, determining the location coordinate of the local electrical activity signal includes periodically determining the location coordinate and displaying a variation of the location coordinate over time. In yet another embodiment, determining the location coordinate includes filtering the sensed RF signals to produce respective narrowband signals, and applying an interferometry calculation to the narrowband signals.

There is further provided, in accordance with an embodiment of the present invention, a method for imaging, including:

directing a plurality of radio frequency (RF) beams toward a target organ from a respective plurality of antenna locations, the plurality of the RF beams including one or more first pairs of the RF beams, each pair including two of the RF beams that impinge on the target organ from opposite directions;

receiving RF signals reflected from the target organ responsively to the RF beams, the RF signals including one or more second pairs of the RF signals engendered respectively by the one or more first pairs of the RF beams;

compensating for local tissue artifacts in the RF signals by jointly processing the RF signals in each of the second pairs; and calculating three-dimensional (3-D) velocity vectors of multiple points in the target organ with respect to the antenna locations using the RF signals after compensating for the local tissue artifacts.

In an embodiment, calculating the 3-D velocity vectors includes evaluating Doppler spectra of the RF signals with respect to the antenna locations for each of the multiple points, identifying dominant spectral components in the Doppler spectra and associating three or more of the dominant spectral components in respective three or more of the Doppler spectra to produce a 3-D velocity vector estimate.

In another embodiment, associating the three or more dominant spectral components includes identifying and discarding false associations between dominant spectral components by comparing the 3-D velocity vector estimate to at least one estimate selected from a group of estimates consisting of previous 3-D velocity vector estimates and 3-D velocity vector estimates of adjacent points in the target organ.

There is also provided, in accordance with an embodiment of the present invention, an imaging system, including:

one or more antennas, which are arranged to direct a plurality of radio frequency (RF) beams toward a target organ from a respective plurality of angles, the plurality of the RF beams including one or more first pairs of the RF beams, each first pair including two of the RF beams that impinge on the target organ from opposite directions;

a receiver, which is arranged to receive via the one or more antennas RF signals reflected from the target organ responsively to the RF beams, the RF signals including one or more second pairs of the RF signals engendered respectively by the one or more first pairs of the RF beams; and a processor, which is arranged to extract local tissue parameters at multiple points in the target organ by jointly processing the RF signals in each of the second pairs and to produce images of the target organ using the extracted local tissue parameters.

There is additionally provided, in accordance with an embodiment of the present invention, an imaging system, including:

a set of antennas, which are configured to define three or more axes of directional reception of radio frequency (RF) signals from a target organ at respective different angles;

a receiver, which is arranged to passively sense, using the set of antennas, the RF signals emitted along the three or more axes due to a local electrical activity signal generated in the target organ; and a processor, which is arranged to determine a location coordinate of the local electrical activity signal based on the sensed RF signals.

There is further provided, in accordance with an embodiment of the present invention, an imaging system, including:

a set of antennas, which are arranged to direct a plurality of radio frequency (RF) beams toward a target organ from a respective plurality of antenna locations, the plurality of the RF beams including one or more first pairs of the RF beams, each first pair including two of the RF beams that impinge on the target organ from opposite directions;

a receiver, which is arranged to receive via the set of antennas RF signals reflected from the target organ responsively to the RF beams, the RF signals including one or more second pairs of the RF signals engendered respectively by the one or more first pairs of the RF beams; and a processor, which is arranged to compensate for local tissue artifacts in the RF signals by jointly processing the RF signals in each of the second pairs, and to calculate three-dimensional (3-D) velocity vectors of multiple points in the target organ with respect to the antenna locations using the RF signals after compensating for the local tissue artifacts.

There is also provided, in accordance with an embodiment of the present invention, a computer software product for imaging, the product including a computer-readable medium, in which program instructions are stored, which instructions, when read by a computer, cause the computer to control one or more antennas to direct a plurality of radio frequency (RF) beams toward a target organ from a respective plurality of angles, the plurality of the RF beams including one or more first pairs of the RF beams, each first pair including two of the RF beams that impinge on the target organ from opposite directions, to receive via the one or more antennas RF signals reflected from the target organ responsively to the RF beams, the RF signals including one or more second pairs of the RF signals engendered respectively by the one or more first pairs of the RF beams, to extract local tissue parameters at multiple points in the target organ by jointly processing the RF signals in each of the second pairs and to produce images of the target organ using the extracted local tissue parameters.

There is additionally provided, in accordance with an embodiment of the present invention, a computer software product for imaging, the product including a computer-readable medium, in which program instructions are stored, which instructions, when read by a computer, cause the computer to configure a set of antennas to define three or more axes of directional reception of radio frequency (RF) signals from a target organ at respective different angles, to passively sense, using the set of antennas, the RF signals emitted along the three or more axes due to a local electrical activity signal generated in the target organ, and to determine a location coordinate of the local electrical activity signal based on the sensed RF signals.

There is further provided, in accordance with an embodiment of the present invention, a computer software product for imaging, the product including a computer-readable medium, in which program instructions are stored, which instructions, when read by a computer, cause the computer to control a set of antennas to direct a plurality of radio frequency (RF) beams toward a target organ from a respective plurality of antenna locations, the plurality of the RE beams including one or more first pairs of the RF beams, each first pair including two of the RF beams that impinge on the target organ from opposite directions, to receive via the set of antennas RF signals reflected from the target organ responsively to the RF beams, the RF signals including one or more second pairs of the RF signals engendered respectively by the one or more first pairs of the RF beams, to compensate for local tissue artifacts in the RF signals by jointly processing the RF signals in each of the second pairs, and to calculate three-dimensional (3-D) velocity vectors of multiple points in the target organ with respect to the antenna locations using the RF signals after compensating for the local tissue artifacts.

There is additionally provided, in accordance with an embodiment of the present invention, a method for radio frequency (RF) ablation, including:

directing a plurality of RF beams toward a target organ from a respective plurality of angles, the plurality of the RF beams including one or more first pairs of the RF beams, each first pair including two of the RF beams that impinge on the target organ from opposite directions;

receiving RF signals reflected from the target organ responsively to the RF beams, the RF signals including one or more second pairs of the RF signals engendered respectively by the one or more first pairs of the RF beams;

extracting local tissue parameters at multiple points in the target organ by jointly processing the RF signals in each of the second pairs; and focusing an ablating signal on an ablation region in the target organ using multiple ablation beams based on the extracted local tissue parameters.

There is also provided, in accordance with an embodiment of the present invention, a radio frequency (RF) ablation system, including:

one or more antennas, which are arranged to direct a plurality of RF beams toward a target organ from a respective plurality of angles, the plurality of the RF beams including one or more first pairs of the RF beams, each first pair including two of the RF beams that impinge on the target organ from opposite directions;

a receiver, which is arranged to receive via the one or more antennas RF signals reflected from the target organ responsively to the RF beams, the RF signals including one or more second pairs of the RF signals engendered respectively by the one or more first pairs of the RF beams;

a transmitter, which is arranged to transmit an ablating signal toward an ablation region in the target organ via the one or more antennas; and a processor, which is arranged to extract local tissue parameters at multiple points in the target organ by jointly processing the RF signals in each of the second pairs, and to cause the ablating signal to be focused on the ablation region in the target organ based on the extracted local tissue parameters.

The present invention will be more fully understood from the following detailed description of the embodiments thereof, taken together with the drawings in which:

BRIEF DESCRIPTION OF THE DRAWINGS

FIG. 4 is a block diagram that schematically illustrates a switching array, in accordance with an embodiment of the present invention;

FIG. 5 is a block diagram that schematically illustrates a digital receiver and exciter unit, in accordance with an embodiment of the present invention;

DETAILED DESCRIPTION OF EMBODIMENTS

Overview

Figure 1A:
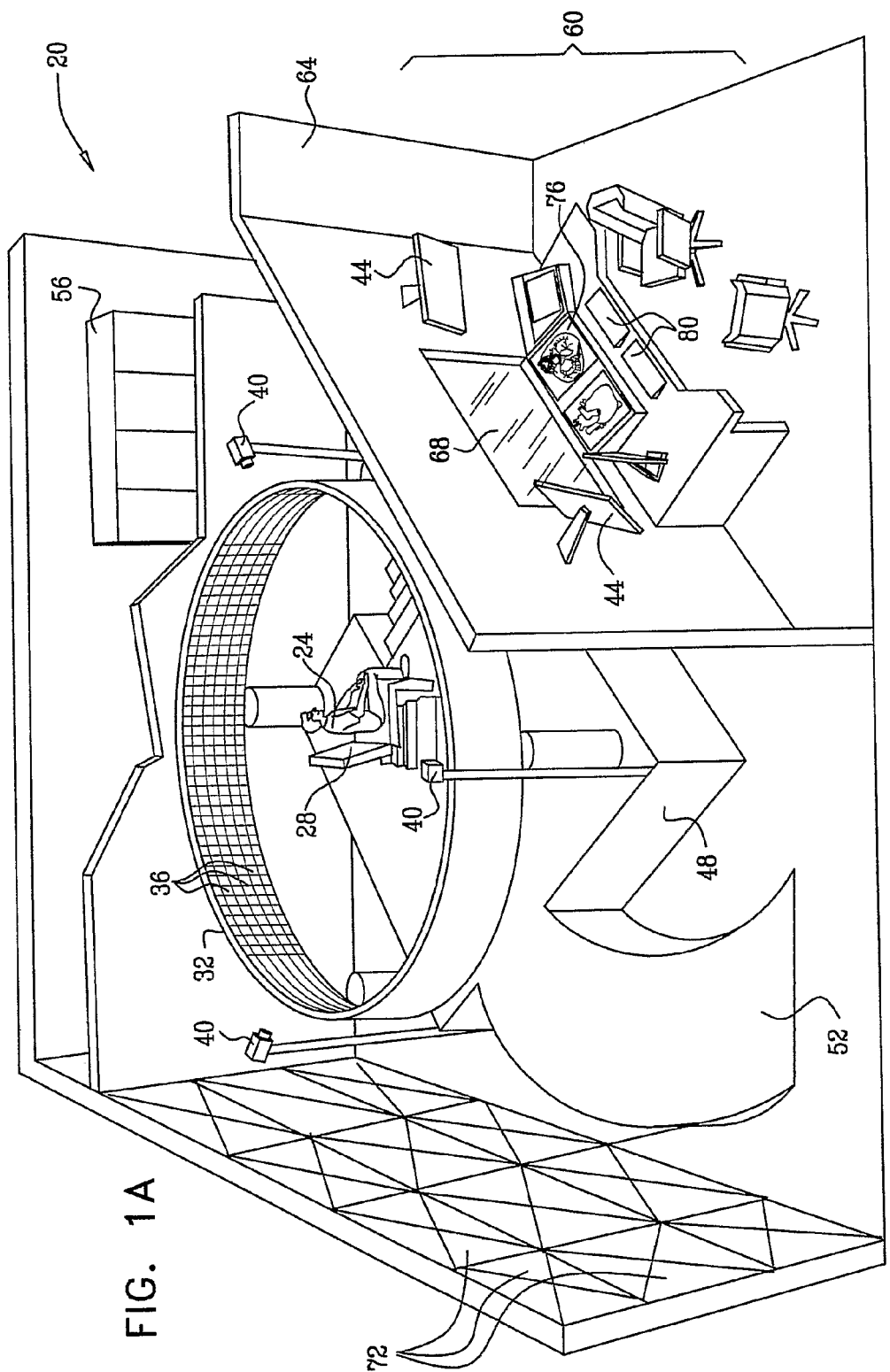
FIGS. 1A and 1B are schematic, pictorial illustrations of radio frequency medical imaging and therapy (RFIT) systems, in accordance with embodiments of the present invention.

The methods and systems described herein provide high-resolution RF imaging and therapy (RFIT) using several operational modes. These modes comprise, for example, active and passive three-dimensional (3-D) imaging modes, 3-D motion vector analysis, and RF therapy modes such as RF ablation, local heating and application of electromagnetic pressure.

In the active imaging mode, a target organ in a patient's body is irradiated with multiple RF beams generated by an antenna array. The antenna array comprises multiple radiating elements. Subsets of elements are selectively actuated to form multiple effective antennas, which transmit and receive multiple radiation beams having different azimuths and heights. From each effective antenna (beam), the system transmits a wideband signal, such as an encoded pulse sequence, having a high temporal resolution.

The transmitted signal interacts with different tissue types in the patient's body. Typically, RF energy is absorbed in tissue and is reflected from transition areas, i.e., interfaces between different tissue types. Part of the transmitted signal is backscattered towards the effective antenna. The magnitude of the backscattered signal as a function of time represents the tissue profile viewed from the particular angle of the beam. For example, homogeneous tissue appears as a substantially uniform, gradually decaying magnitude. Tissue interfaces appear as temporal peaks due to the associated reflection.

The RFIT system receives and analyzes the backscattered signals in order to image the target organ. The system may use multiple analog-to-digital (A/D) converters that sample the signal at incremental time offsets in order to enhance the range resolution of the acquired samples. The system compensates for different artifacts and measurement distortions, such as local tissue attenuation, local variations in light velocity (i.e., local time delay), and signal dispersion. Artifact compensation is performed by jointly analyzing pairs of beams that irradiate the target organ from opposite directions. These compensation methods further improve the achievable spatial resolution of the system.

After compensating for the different artifacts, different local tissue parameters, such as attenuation, reflection, time delay, as well as local dielectric properties, are extracted from the measurements.

In some embodiments, measurements are performed using multiple beam pairs from multiple directions. The data collected by the multiple beams, after artifact correction, is reconstructed in both azimuth and height, to produce a 3-D representation of the target organ. The extracted tissue properties of the target organ are displayed in two or three dimensions, so as to enable tissue differentiation and classification with high spatial and temporal resolution. The system provides both anatomical and functional tissue information.

Unlike some known methods and systems, such as some of the known imaging modalities cited above, the RFIT system can accurately determine the tissue type (e.g., blood, muscle, nerve, bone or fat) for each point in space as a function of time, based on the measurement and calculation of multiple local tissue parameters.

In order to verify the expected performance of the disclosed methods and systems, a series of experiments and computer simulations were conducted, as will be described below. The methods and systems described herein are expected to achieve a spatial resolution on the order of 1 mm per axis and a temporal resolution on the order of 100 Hz (10 ms). This performance is significantly superior to the resolution of known systems, such as the systems and modalities cited in the background section above. As a result, the ability of a physician to diagnose and treat various medical conditions is significantly improved.

The methods and systems described herein provide enhanced imaging performance of dynamic organs, such as the heart or lungs, because of the high temporal resolution. Unlike some known imaging modalities, a temporal resolution on the order of 100 Hz enables real-time cardiac imaging. Furthermore, the high temporal resolution eliminates the need for gated imaging, which is typically required in known imaging methods having slower refresh rates.

In the passive imaging mode, the system passively senses the electrical activity of neurons, muscle cells and/or endplates. In other operational modes, the system can perform high-resolution RF ablation, local heating and/or apply RF-induced electromagnetic pressure to selected tissue.

In some embodiments, a suitable contrast agent can be administered to the patient prior to imaging, so as to enable organ-specific functional imaging. Different system configurations may support any desired subset of the operational modes.

Unlike some known RF imaging methods and systems, which are limited to relatively shallow penetration depths (e.g., breast imaging), embodiments of the present invention achieve high performance imaging in applications requiring deep RF penetration, such as cardiac imaging.

System Description

FIG. 1A is schematic, pictorial illustration of a radio frequency medical imaging and therapy (RFIT) system 20, in accordance with an embodiment of the present invention. The description that follows refers mainly to the active imaging mode, for the sale of clarity. The other operational modes and the system configurations supporting them are described further below.

A patient 24 sits on a chair 28, which is located in the middle of a cylindrical antenna array 32. The antenna array comprises multiple antenna elements 36, which are selectively combined and actuated to form multiple effective antennas. The effective antennas transmit and receive RF beams having different orientations to and from the patient's body, in order to image and/or apply treatment to a target organ or tissue. In order to perform RF ablation, local heating or generate RF-induced pressure, however, some or all of antenna elements 36 transmit in unison towards a certain focal point. Although the embodiments described below mainly address cardiac imaging applications, the methods and systems described herein can be used to image and treat any other suitable target organ and tissue type.

In the exemplary system configuration of FIG. 1A, array 32 has a diameter of approximately 4 m and a height of approximately 80 cm. Six hundred thirty elements 36 are distributed around the cylinder perimeter, and the array has a height of forty elements. Thus, in total, the array comprises twenty-five thousand two hundred antenna elements. In alternative embodiments, array 32 may comprise a lower or higher number of elements and may have any other suitable shape or dimensions. In some embodiments, the system comprises one or two additional dome-shaped antenna arrays (not shown in the figure), which are positioned above and/or below the patient. The additional arrays further improve the spatial resolution of the system, particularly when performing RF ablation.

Antenna elements 36 may comprise any suitable wideband radiating element known in the art, such as flared-notch based elements, spiral or helical elements and horn-based elements. In some embodiments, array 32 may comprise elements transmitting in different polarizations, so as to enable the system to perform polarization-dependent parameter measurements. In some embodiments, elements 36 are active elements, which comprise power amplifiers for transmission, as well as low noise amplifiers and multiple A/D converters for reception.

Chair 28 typically comprises materials that cause little distortion to the RF radiation, i.e., materials having low reflectance and absorption. The chair may comprise, for example, polystyrene foam, wood, artificial leather and cloth. Other objects, such as various medical and surgical tools and instruments, may be present in the vicinity of the patient. These objects should also comprise RF transparent materials or be covered with RF absorbing material.

Typically, the target organ to be imaged should be positioned substantially at the center of the cylindrical antenna array, in both horizontal and vertical dimensions. For this purpose, chair 28 is typically adjustable and may also recline so the patient can lie horizontally. The chair may have multiple adjustable degrees of freedom. In some embodiments, video cameras 40 are used for accurately positioning the patient at the center of the cylinder. Cameras 40 are mounted at different angles with respect to chair 28. Each camera is mounted so that the center of its field of view points to the center of the cylindrical array. The images produced by cameras 40 are displayed on one or more positioning displays 44. In order to position the patient correctly, chair 28 is remotely or locally adjusted until the region of interest (e.g., the patient torso) is seen at the center of the field of view of all cameras.

Array 32 may be mounted on an elevated platform 48. Some elements of system 20, such as signal generation and reception circuitry, should be located near the antenna array in order to minimize RF losses. Such system elements may be located underneath the elevated platform. A ramp 52 enables wheelchair or gurney access to the platform. Other system elements, such as signal processing elements, can be located in a rack 56, located further away from array 32. Typically, a spacious area is left around the patient, so as to allow easy access to the patient by staff and equipment. For example, RF imaging and therapy can take place in parallel to other procedures, such as catheterization and imaging using other modalities.

System 20 is controlled and operated from a control station 60, typically separated from array 32 by an RF absorbing wall 64. A window 68 comprising RF absorbing material may be used for viewing the patient from the control station. The RF absorbing wall and window help to protect staff from RF radiation. RF leakage into and out of system 20 can also be reduced by covering external walls with radiation absorbing material, such as RF absorbing tiles 72. The room housing system 20 should be air-conditioned, in order to dissipate the heat produced by the RF energy, particularly when performing RF ablation.

Control station 60 comprises one or more imaging displays 76, which display the imaged target organ and other relevant information. The control station also comprises input devices 80, such as a keyboard, mouse and/or trackball, for providing input and controlling the system.

Figure 1B:
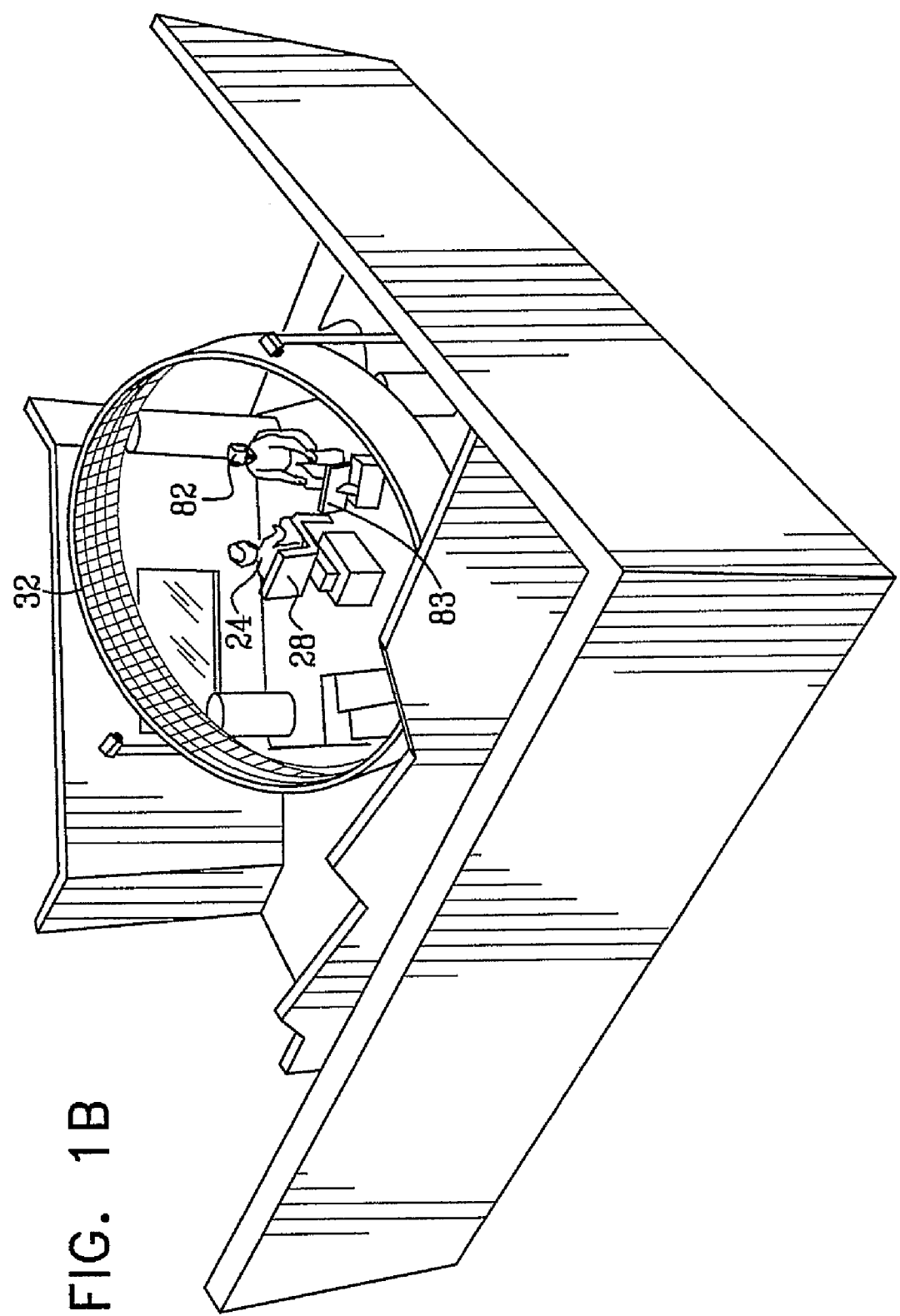

FIG. 1B is a schematic, pictorial illustration of an RFIT system, in accordance with an alternative embodiment of the present invention. In the system configuration of FIG. 1B, cylindrical antenna array 32 is tilted at an angle typically in the range of 30-50°. Chair 28 is positioned so that the area of interest, in the present example the torso of patient 24, is located at the center of the cylinder.

The configuration of FIG. 1B is particularly suitable for applications in which staff and/or equipment are present in the vicinity of the patient, but their effect on the RF radiation should be minimized by positioning them outside the beam paths. For example, this configuration may be used in different intra-operative imaging applications, such as catheterization procedures.

In the present example, a physician 82 sits or stands below the elevated area of the array, by the patient's feet. A display 83 displays the data acquired by the system to the physician. In some embodiments, radiation absorbing clothing can be worn by the physician to minimize radiation exposure.

Operational Modes

System 20 supports several operational modes for imaging and/or therapy. Some system configurations may support all modes, whereas other configurations may support only a single mode or a subset of the modes.

In some embodiments, the system supports an active imaging mode, in which the target organ is scanned with multiple beams. In the present example, the beams have horizontal beam widths of approximately 15° and vertical beam widths of approximately 4°, although other radiation patterns can also be used. Using the exemplary array dimensions and geometries shown in FIGS. 1A and 1B above, these beam widths are suitable for irradiating the patient torso. In order to produce such beam widths, each effective antenna is approximately 15 cm wide and 50 cm high. Assuming antenna elements 36 are spaced 2 cm apart, each effective antenna has approximately seven elements in the horizontal dimension and twenty-five elements in the vertical dimension.

The system measures multiple tissue parameters at multiple locations in the target organ and displays them in three dimensions. Typically, the system directly measures three parameters for each location, namely the local RF attenuation, local reflection coefficient and local time-delay caused by the decreased light velocity in tissue with respect to free space. The measured parameters, as well as the collected raw data, may also be used for evaluating dielectric tissue properties, such as the local complex permittivity and local conductivity of the tissue.

Each of the parameters described above can be evaluated using the entire system bandwidth, or separately in multiple sub-bands. Parameters can also be evaluated for different polarizations. Each parameter, or a combination of parameters, can be displayed in 3-D. For example, when performing cardiac imaging, the system can measure and display the local conductivity along the conduction pathways within the heart. As another example, valve calcification in the heart can be accurately detected based on a 3-D measurement and display of local permittivity.

The multiple tissue parameters can be jointly analyzed in order to accurately and reliably classify the tissue type, e.g., bone, muscle, fat or blood, at each location in the target organ. Using this analysis, a high-resolution display of the target organ, with each tissue type clearly marked and differentiated, can be provided to the physician. In the active imaging mode, the entire heart can be imaged at a typical frame rate of 100 Hz, without gating. The spatial resolution can reach 2 mm, and often 1 mm or better.

In some embodiments, certain dynamic mechanical properties of the target organ can be evaluated by tracking frame-to-frame variations in the active imaging mode. This sub-mode is referred to herein as tissue tracking. For example, tissue tracking can estimate the cardiac wall motion velocity, as well as the local strain and local strain-rate. These properties are usually expressed as 3-D vectors.

Tracking inter-frame variations may involve known image processing techniques, such as optic flow methods. Additionally or alternatively, anatomical landmarks can be identified in the images, either manually or automatically. The variation in the coordinates of these landmarks can then be tracked in different frames.

In some embodiments, a contrast agent can be used during active imaging. The contrast agent is used to produce irregular values of one or more of the measured parameters. For example, a contrast agent may comprise a highly reflective substance, such as a ferrite-based substance. Some contrast agents target a specific organ or tissue type, so as to allow highly-specific functional imaging. For example, organ-specific agents can be used for myocardial perfusion estimation, kidney performance evaluation and liver performance evaluation.

In some embodiments, system 20 supports a 3-D motion vector analysis mode, which measures the local motion vector for each location in the scanned target organ (e.g., the local blood velocity), as a function of time. In this mode, the system analyzes multiple reception beams simultaneously, and measures the Doppler shift with respect to each beam. The Doppler shift, as measured for each point in space with respect to several reference points, is used to determine the dominant velocity vector for each such point as a function of time. The full Doppler spectrum as a function of time and space may also be calculated for a particular component of the vectors.

Using the motion vector analysis mode, it is anticipated that imaging of the entire human heart can be performed at a frame rate on the order of 20 Hz, without gating. The spatial resolution in each axis is expected to be on the order of 1 mm. The resolution of velocity measurements in each beam is expected to be approximately 0.3 m/s, and the Nyquist frequency (i.e., maximum unambiguous velocity) is expected to be approximately 3 m/s.

In some embodiments, system 20 supports a non-invasive RF ablation mode. In this mode, the antenna array focuses RF energy to a small region in the target organ in order to increase the local temperature by a factor on the order of 20° C. The local temperature can be measured in the active imaging mode. By combining the two modes, the system can stabilize the temperature in the target spot. RF ablation can be used for removing tumors and cancerous cells, as well as for performing non-invasive surgical operations such as internal hemorrhage reduction.

Typically, RF ablation in system 20 is performed in parallel to active imaging. Unlike known ablation methods, which use different modalities for imaging and ablation, in system 20 no registration is usually needed between the coordinate systems used for imaging and for ablation.

The spatial resolution of the ablation mode is expected to be approximately 6 mm per axis, at the 3 dB points of the ablation region. Using higher frequency bands may allow improving the spatial resolution by a factor of about two. When ablation is guided by active imaging, the frame rate is expected to be approximately 50 Hz, and the imaging spatial resolution is expected to be around 1 mm per axis.

Simultaneous operation of the RF ablation mode with the tissue tracking mode enables non-invasive ablation of moving organs, such as the destruction of ectopic regions in the cardiac muscle and the removal of lung cancer cells. When RF ablation is combined with tissue tracking, the system adaptively adjusts the ablation region with a refresh rate comparable to the imaging frame rate.

In some embodiments, system 20 can be used to apply electromagnetically-induced pressure to target tissue. In some cases, applying instantaneous high-power electromagnetic pressure to a nerve pathway may induce an action potential either directly, or due to thermal effects. Thus, applying electromagnetic pressure may help to control the innate frequency of different regions within the cardiac conduction system, so as to achieve a stable sinus rhythm. The pacing of other visceral organs, such as the gastro-intestinal system, may also be affected by electromagnetic pressure.

Additionally or alternatively, system 20 can be used to apply local heating to tissue. Local heating can be used, for example, to treat stressed muscles and to speed the natural healing of bruised or inflamed areas. In the local heating mode, a target region can be defined and visualized using the active imaging mode. The system can then locally heat the selected region by applying low-power RF energy to the region.

In some embodiments, system 20 performs high-speed passive imaging of electrical activity in the target organ. Various cells in the human body, such as nerve and muscle cells, are known to show substantial electrical activity. This activity may sometimes be detected non-invasively by a sensitive receiver. In the passive imaging mode, system 20 triangulates the signals sensed by multiple reception beams, in order to determine the location of the electrical activity. The passive imaging mode is expected to reach a temporal resolution of approximately 1 μs and a spatial resolution of approximately 1 mm. This performance level should enable the system to display electrical signals as they pass through various physiological systems.

Data processing in system 20 can be performed either in real-time, i.e., during data acquisition, or off-line, i.e., after data acquisition is completed. In the active and passive imaging modes and in the motion vector analysis mode, data processing may be performed either in real-time or off-line. In the RF therapeutic modes, data processing is typically performed in real time in order to provide imaging guidance to the therapeutic procedure.

System Components

Figure 2:
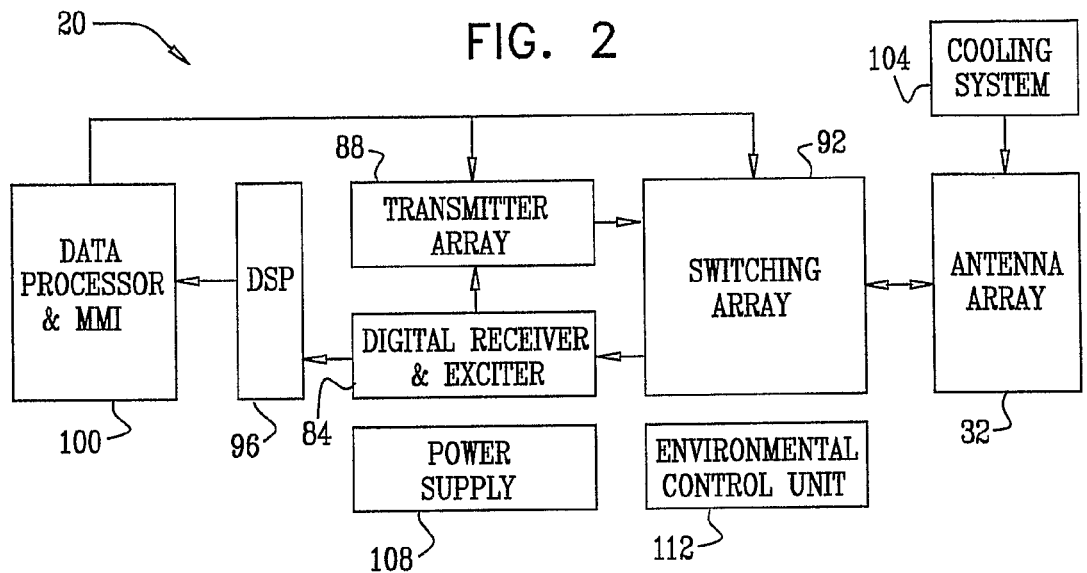
FIG. 2 is a block diagram that schematically illustrates a RFIT system, in accordance with an embodiment of the present invention.

FIG. 2 is a block diagram that schematically illustrates RFIT system 20, in accordance with an embodiment of the present invention. The system comprises a digital exciter and receiver unit 84, which generates the signals used in the various imaging and therapy modes. The signal produced by the exciter is split into multiple signals and amplified by a transmitter array 88. The amplified signals are distributed to individual antenna elements 36 in antenna array 32 by a switching array 92, so as to form the appropriate radiation beams. The signals are transmitted towards the target organ by array 32.

The backscattered RF radiation is received by array 32. Switching array 92 selects the appropriate subset of elements 36 corresponding to the currently-received beam. The signal corresponding to the specific beam is received by a digital receiver in unit 84. The signal produced by the receiver is processed by a digital signal processor (DSP) unit 96. DSP unit 96 typically performs computationally-intensive calculations, such as operations that are repeated many times. These calculations may comprise, for example, compensation for artifacts and measurement distortions and 3-D image reconstruction.

A data processor and man-machine interface (MMI) unit 100 manages the various real-time processes performed by system 20 and controls other system elements, such as transmitter array 88, digital receiver and exciter 84 and switching array 92. The management of real-time processes may comprise mode selection, calculation of parameters to be used by DSP unit 96 and other system elements, as well as general system timing.

Unit 100 also interacts with the user, in order to accept user input and commands. In some embodiments, unit 100 comprises a video/display processor (not shown in the figure), which performs the transformations that translate the time-dependent 3-D images and calculated parameters, generated by DSP unit 96, to the desired viewing configurations presented on displays 76 and 83. In some embodiments, the video/display processor may also perform the final tissue classification, i.e., determining the tissue type for each point in space based on the 3-D images. Additionally or alternatively, the video/display processor may carry out tissue tracking.

Typically, DSP 96 and unit 100 comprise general-purpose or customer off the shelf computers, which are programmed in software to carry out the functions described herein. The software may be downloaded to the computers in electronic form, over a network, for example, or it may alternatively be supplied to the computers on tangible media, such as CD-ROM. DSP 96 and unit 100 may be implemented in a single computing platform or in separate platforms. Some or all of the functions of DSP unit 96 may also be implemented in hardware.

In some embodiments, in particular when performing passive imaging, the thermal noise level of antenna array 32 should be reduced. For this purpose, system 20 may comprise a cooling system 104, which cools antenna array 32, switching array 92 and/or the receiver in unit 84. System 20 is powered by a power supply 108. Appropriate environmental conditions, e.g., temperature and humidity, are maintained by an environmental control unit 112.

Figure 3:
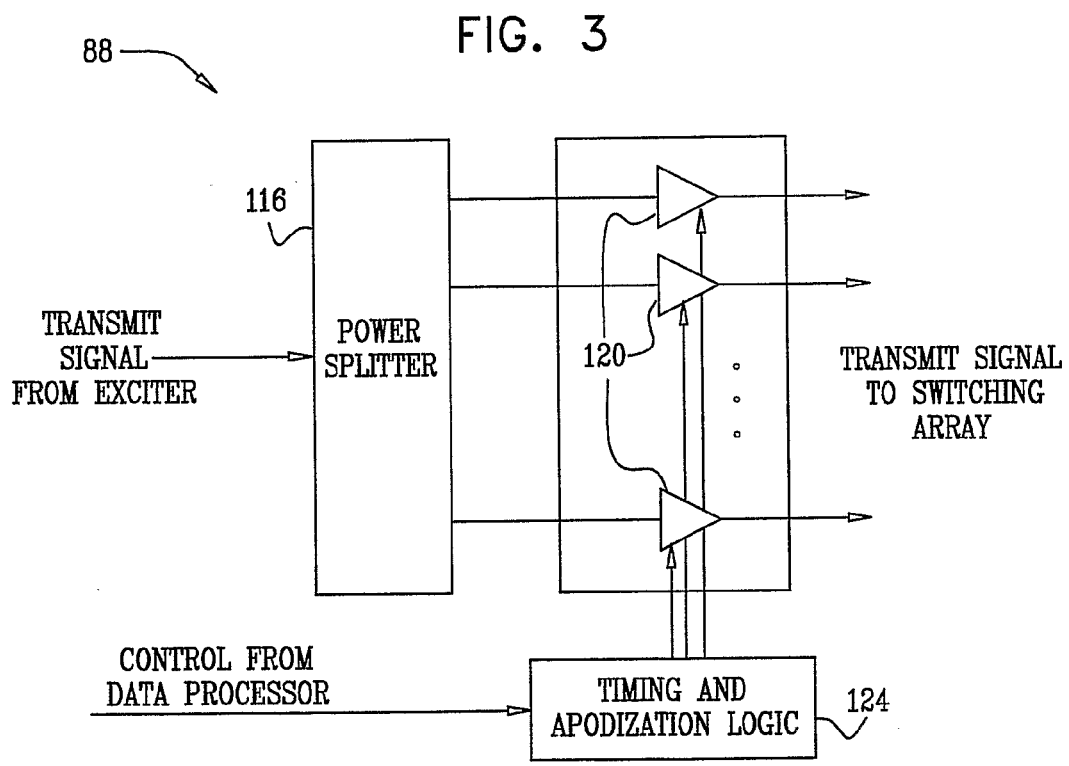
FIG. 3 is a block diagram that schematically illustrates a transmitter array, in accordance with an embodiment of the present invention.

FIG. 3 is a block diagram that schematically illustrates transmitter array 88, in accordance with an embodiment of the present invention. The signal produced by the exciter in unit 84 is split by a power splitter 116 and amplified by multiple power amplifiers 120. The amplified signals are provided to switching array 92. As will be shown below, the transmitted power of each effective antenna is set to around 3 kW peak power and 350 W average power. Assuming each effective antenna comprises 25×7=175 elements, the peak power of each amplifier 120 is approximately 17 W and the average power is 2 W. These power levels are readily achievable using known solid-state devices.

Each amplifier 120 produces a signal that will ultimately drive a particular element 36 in the currently-used effective antenna. Thus, the number of amplifiers 120 in the transmitter array should match the number of elements in the effective antenna. In alternative embodiments, a single amplifier can be allocated to a group of elements in the effective antenna.

In the RF ablation mode, the number of elements assigned to a particular amplifier may depend on the desired ablation region size and on the ability to control the antenna array focal point. In the passive imaging mode, the transmitter array is not used.

In some embodiments, the beam of the effective antenna is focused and shaped by applying different weights and/or different timing offsets to the different elements. This process is commonly referred to as apodization. In these embodiments, transmitter array 88 comprises a timing and apodization module 124, which is controlled by the data processor. Module 124 adjusts the timing, gain and/or phase of amplifiers 120, in accordance with the apodization scheme used. In some embodiments, encoding of the transmitted pulse sequence, a function that is described in detail further below, is also carried out by module 124.

FIG. 4 is a block diagram that schematically illustrates switching array 92, in accordance with an embodiment of the present invention. Switching array 92 is connected to antenna array 32. An exemplary effective antenna 128 is shown in the figure. On transmission, switching array 92 accepts the signals from transmitter array 88 and routes them to the appropriate elements 36 in antenna array 32, in accordance with the currently-used effective antenna. On reception, switching array 92 routes the signals received by the elements of the currently-used effective antenna to the receiver in unit 84.

Switching array 92 comprises a switch matrix 132, which selects the appropriate subset of elements 36. The switch matrix is controlled by the data processor of unit 100. The switching array further comprises multiple duplexers 136. On transmission, the duplexers isolate the transmitted signals from the receiver. In some embodiments, the geometry and pulse repetition frequency (PRF) of the system are configured so that transmission and reception do not occur simultaneously. In these embodiments, T/R switches or circulators may be used instead of duplexers 136.

The operation and/or configuration of the switching array may vary for different operational modes of system 20. For example, in the active imaging mode, a single receiver channel may be assigned to each element of the currently-used effective antenna, to a group of elements, or to the entire effective antenna. In the motion vector analysis mode, a single transmit beam and several (e.g., 10) receive beams are used. The receive beams are often narrower than in the active imaging mode, therefore the effective antennas comprise a higher number of elements 36. During RF ablation, most or all elements participate in the transmission, and no reception is performed. In the passive imaging mode, no transmission is carried out, and several receive beams are used, either alternately or simultaneously.

In order to achieve the desired frame refresh rate, system 20 performs high-speed beam switching, typically on the order of 9 MHz (i.e., scanning of 9,000,000 beams per second). The switching elements in switch matrix 132 should support this high switching speed. For example, PIN-diode switches, such as the S9H-79-3 device produced by GT Microwave, Inc. (Randolph, N.J.), can be used for this purpose. These devices have a 30 ns switching time. Further details regarding these PIN-diode switches are available at www.gtmicrowave.com.

FIG. 5 is a block diagram that schematically illustrates digital receiver and exciter unit 84, in accordance with an embodiment of the present invention. Unit 84 comprises an exciter 140, which produces the pulsed signal waveforms used for transmission and provides the signals to transmitter array 88. As shown in FIG. 2 above, on reception, unit 84 accepts the received signals from elements 36 of the currently-used effective antenna via switching array 92. The signals are combined using a power combiner 142.

A correlator module 144 correlates the received signal with the expected signal, i.e., the signal waveform produced by the exciter. The pulse shape of the transmitted pulses is typically selected so that its temporal point spread function (PSF) has low sidelobes. In some embodiments, module 144 performs additional functions such as matched filtering, down-conversion to a suitable baseband or intermediate frequency (IF) and/or pulse de-compression. Module 144 may also apply time-dependent gain control (TGC) to the signal.

In alternative embodiments, pulse de-compression can be performed using suitable software or digital hardware after the signal is digitized. Signal down-conversion may also be performed on the digitized signal. In such configurations, the signal should be digitized at a sampling rate corresponding to the highest radio frequency used (e.g., 18 GHz).

As will be described in greater detail below, the range resolution of the system is achieved by sampling (digitizing) the signal using multiple analog-to-digital (A/D) converters that sample the signal at incremental time offsets. For this purpose, the signal produced by module 144 is split by a 1:15 power splitter 146. The fifteen outputs of the power splitter are delayed by fifteen delay lines 148.

In the exemplary system configuration described herein, the signal produced by module 144 enables a raw spatial resolution of 1.5 cm. Delay lines 148 divide this range into 15 intervals. In other words, the delay difference between successive delay lines is equivalent to a 1 mm range. The outputs of the delay lines are sampled by fifteen synchronized A/D converters 150. The sampled signals are provided to DSP unit 96.

The exemplary configuration of FIG. 5 is typically suitable for the active imaging mode. In the passive imaging mode, the system does not transmit. In this mode, module 144 correlates the received signal with a synthetically-produced signal that approximates the signal waveform that is expected to be produced by the target tissue. In the RF ablation mode, exciter 140 produces the ablating signal waveform, and the receiver is used only when performing imaging. In the motion vector analysis mode, the target organ is imaged simultaneously by several beams. An exemplary receiver configuration suitable for this mode is described in FIG. 12 further below.

In alternative embodiments, some of antenna elements 36 can be defined as transmit-only elements, and other elements may be defined as receive-only elements. Such configurations reduce the number of duplexers and cables, and simplify the system calibration. Hybrid configurations in which some elements are transmit-only, some are receive-only and some perform both transmission and reception, are also feasible.

In some embodiments, the system configuration can be simplified by relaxing some of the system requirements. For example, the system can be defined to support only a single operational mode or a small subset of modes. Defining the system for a smaller penetration depth and/or slower refresh rate can also simplify the system. For example, when using a slower refresh rate, the system can use transmitted signals having simpler waveforms, such as waveforms based on stepped frequency, linear frequency modulation, complementary coding and other phase coding methods. The system can use longer pulse sequences in conjunction with these waveforms.

In alternative embodiments, the system can perform mechanical antenna scanning instead of electronic scanning. For example, a single antenna can be steered mechanically around the patient in one or more axes, so as to produce the multiple beams needed for imaging. As another example, a pair of antennas can be positioned on opposite sides of the patient and steered mechanically around the patient, forming pairs of beams on opposite sides of the patient. Alternatively, two or more antenna pairs can be used. Further alternatively, the antenna or antennas can be stationary, and the patient can be moved and/or rotated with respect to the antennas.

Additionally or alternatively, the distance between the antenna and the patient can also be changed incrementally by moving either the antenna or the patient. Using multiple distances between the antenna and patient is equivalent to using multiple A/D converters having incremental time offsets. Spherical scanning, or any other suitable scanning geometry, can be used instead of cylindrical scanning, when using either mechanical or electrical scanning.

In system configurations based on mechanical scanning, the number of antennas and amplifiers is significantly reduced, and the switching array can be significantly simplified or altogether eliminated. Such configurations may be particularly suitable for applications that do not involve hospitalization, such as in dentistry, plastic surgery, opthalmology and orthopedic applications. Configurations in which the antennas are stationary and the subject is moved may be useful in experimental and non-medical applications, such as in animal experiments.

Spatial Resolution

The spatial resolution expected to be achieved by system 20 in the active imaging mode is on the order of 1 mm per axis. In particular, when processing the backscattered signal of a certain beam, the system has a range resolution of 1 mm. This resolution level is achieved by a combination of (1) using a wideband transmitted waveform having a range resolution of ~1.5 cm, and (2) dividing the 1.5 cm resolution into 1 mm effective range gates by processing the received signal using fifteen A/D converters having incremental time offsets.

The transmitted signal produced by exciter 140 comprises a sequence of narrow pulses (narrow in time and wide spectrally). Each pulse has a bandwidth of approximately 10 GHz, i.e., a pulse width of approximately 0.1 ns. Typically, the spectral content of the pulse covers the range of 8-18 GHz. In alternative embodiments, higher bandwidths, such as 6-25 GHz, may also be feasible.

In order to improve signal-to-noise (SNR) ratio, exciter 140 produces a sequence of sixty-four successive pulses. The sequence is phase-encoded, i.e., each pulse in the sequence is given a certain phase shift. In the present example, bi-phase encoding is used, in which the phase shifts are either 0° or 180°. Alternatively, any other suitable encoding scheme can be used. On reception, the received pulse sequence is correlated with a reference sequence, so as to achieve the desired pulse compression gain.

Narrow, wideband pulses can be produced, for example, by chopping a narrowband signal whose frequency approximately matches the desired transmit carrier frequency. Alternatively, a baseband signal can be chopped and then up-converted to the desired transmit frequency. High speed chopping can be performed, for example, using step recovery diodes (SRD). For example, Aeroflex/Metelix Inc. (Sunnyvale, Calif.) offers a silicon SRD device denoted MMDB30-B11, which can be used for this purpose. These diodes are capable of generating 30 ps pulses. Further details are available at www.aeroflex-metelics.com.

Since the recovery time of SRD devices is relatively long, a sequence of short pulses can be generated by multiple SRD devices in parallel, which are actuated sequentially. Each SRD generates a single pulse in the sequence at the appropriate timing.

Figure 6A:
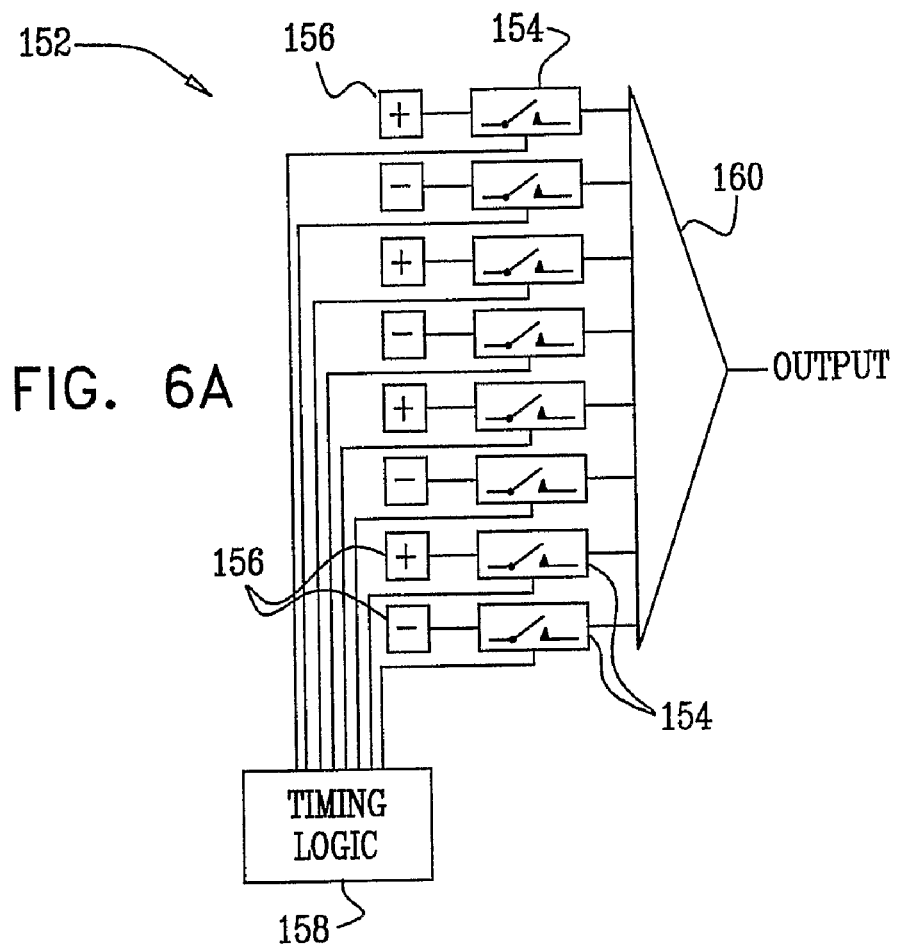
FIGS. 6A and 6B are diagrams that schematically illustrate a pulse generation circuit, in accordance with an embodiment of the present invention.
Figure 6B:
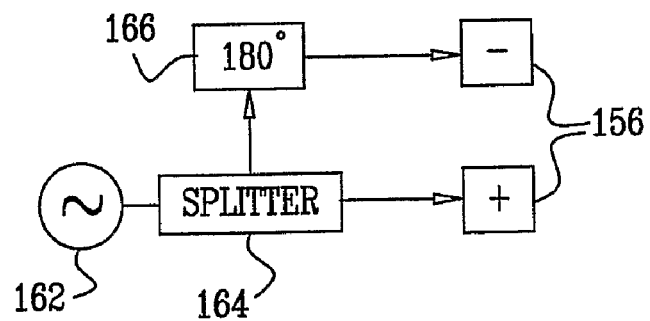

FIGS. 6A and 6B are diagrams that schematically illustrate a pulse generation circuit 152, which may be used by exciter 140 to generate the transmitted pulse sequences, in accordance with an embodiment of the present invention. Circuit 152 of FIG. 6A comprises a sequence of SRD-based switches 154. Circuit 152 shows only eight switches for the sake of simplicity, however similar circuits having different numbers of switches can be used to generate pulse sequences having any desired number of pulses. Each switch 154 has an input 156, which accepts a phase-encoded RF signal. In the present example, bi-phase encoding is used. The input to a switch whose pulse is encoded with a 0° phase shift is marked "+", and the input to a switch whose pulse is encoded with a 180° phase shift is marked "−". The switches are actuated sequentially by a timing logic circuit 158. The SRD outputs are combined using a combiner 160 to produce the desired pulse sequence.

FIG. 6B shows an exemplary circuit for generating the phase-encoded RF signal used as input to the different SRD switches, in accordance with an embodiment of the present invention. An oscillator 162 generates a continuous sinusoidal signal at the desired transmit frequency. The output of oscillator 162 is split by a power splitter 164. One output of the splitter is provided to the SRD stages encoded with a 0° phase shift (the stages marked with "+" in FIG. 6A). The other output of the splitter is phase-inverted using a 180° phase shifter 166, and provided to the SRD stages encoded with a 180° phase shift (the stages marked with "−").

Figure 7:
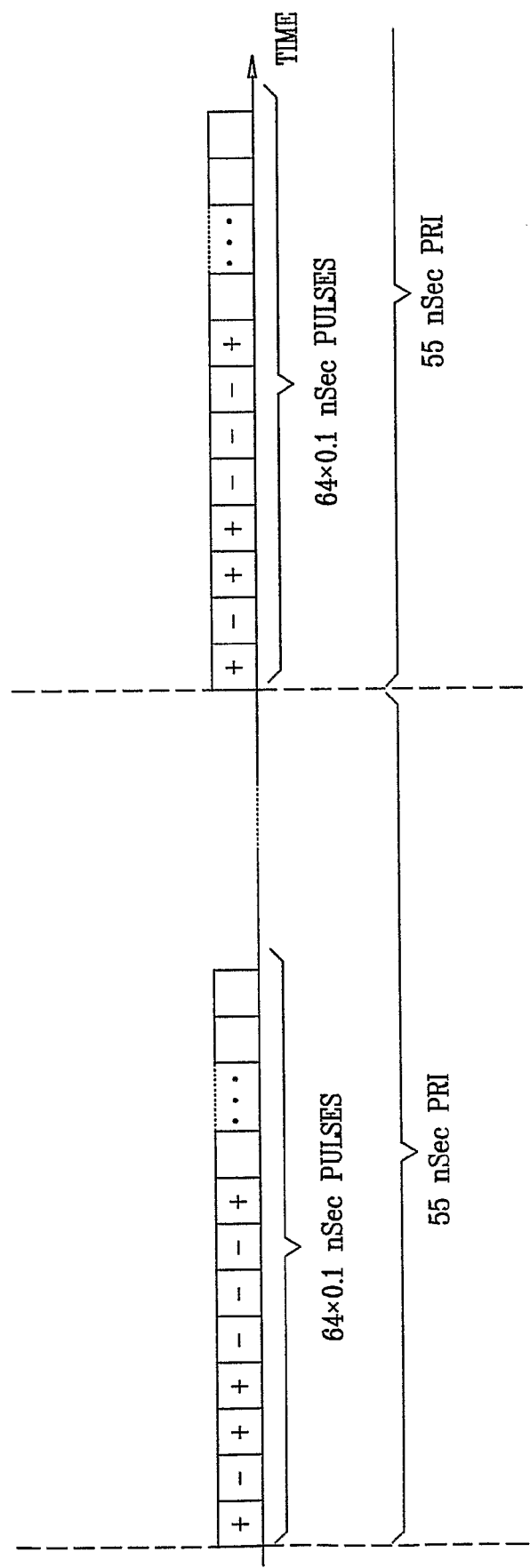
FIG. 7 is a diagram showing transmitted pulse sequences, in accordance with an embodiment of the present invention.

FIG. 7 is a diagram showing transmitted pulse sequences generated by exciter 140, in accordance with an embodiment of the present invention. In the present example, exciter 140 transmits sequences of 64 phase-encoded pulses. Each pulse is 0.1 ns wide, so that the overall transmitted signal has a length of 6.4 ns. The exciter transmits pulse sequences at a pulse repetition interval (PRI) of 55 ns. This PRI corresponds to a two-way range of over 8 m in free space, significantly more than the radius of antenna array 32, thus avoiding range ambiguity. In some embodiments, two or more pulse sequences are transmitted per beam. In these embodiments, for each beam position, the data of each range gate may be integrated over the different pulses in order to enhance SNR. The 55 ns PRI is selected in order to achieve a temporal resolution of 100 Hz, as will be described in greater detail in FIG. 10 below.

As noted above, the reflected signal is sampled by fifteen parallel A/D converters having incremental time offsets equivalent to 1 mm. The fifteen A/D converters effectively divide the 1.5 cm range gates achieved by the wideband pulses into effective range gates of 1 mm. In some embodiments, DSP unit 96 solves a set of linear equations based on the outputs of the fifteen A/D converters, and evaluates the received signal with a resolution of 1 mm. The DSP unit may apply known deconvolution methods for this purpose. This process is typically performed separately for each pulse in the pulse sequence. In some embodiments, after processing each pulse, DSP unit 96 integrates the data for each range gate over the sixty-four pulses in the sequence in order to improve the measurement SNR.

Module 144 in the receiver performs time-dependent gain control (TGC) prior to digitization of the signal, in order to provide sufficient dynamic range at the A/D converters. The TGC process typically uses a fixed or pre-calibrated function that specifies the attenuation as a function of range. The function may be evaluated by occasionally transmitting a narrow calibration beam and measuring the attenuation as a function of range. Typically, the TGC process provides coarse gain control, and an additional fine gain control process is performed digitally, after the signal is sampled by the A/D converters.

The description above refers to a cardiac imaging application, which is highly-dynamic and imposes harsh refresh rate requirements. For organs other than the heart, a 100 Hz refresh rate may not be necessary. In these cases, longer pulse sequences, which may comprise up to 1000 pulses or more, may be used. Using long pulse sequences significantly increases the achievable penetration depth.

Parameter Extraction and Measurement Artifact Compensation

The reflected signal measurements performed by system 20 are often distorted as a result of the different physical properties of the imaged tissue. Different tissue types differ from one another, and from free space, by their light velocity, local attenuation and signal dispersion properties. In some embodiments, system 20 compensates for these artifacts in order to achieve high spatial resolution.

As noted above, system 20 scans the target organ using multiple beams from multiple directions. In some embodiments, the system compensates for tissue artifacts by jointly-analyzing the reflections measured by pairs of beams that image the target organ from opposite directions.

Figure 8A:
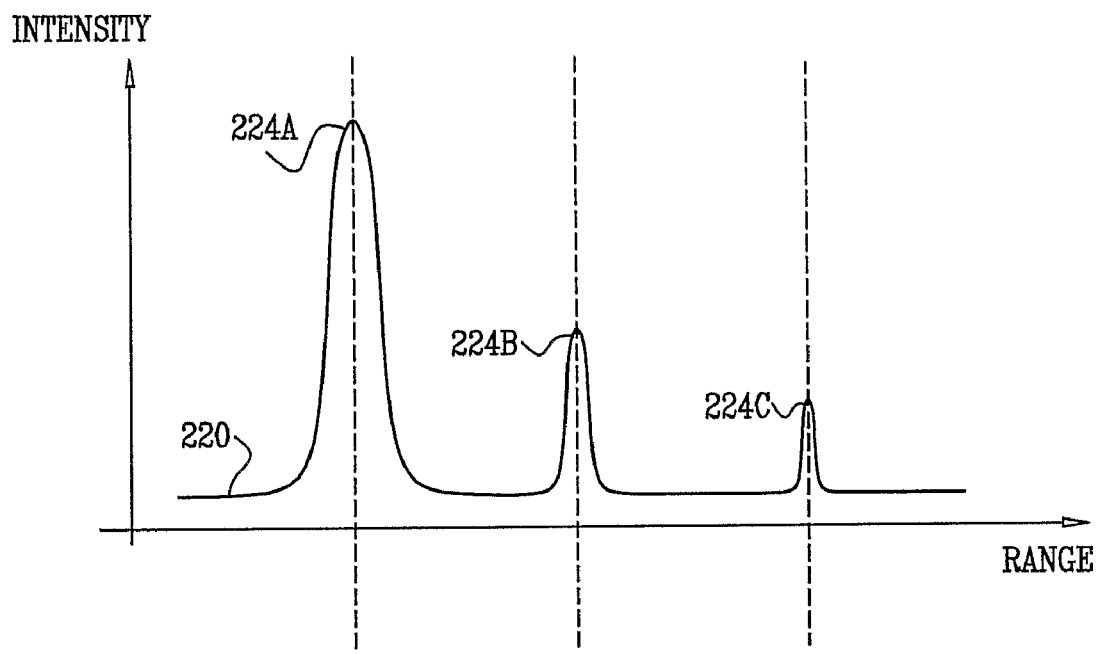
FIGS. 8A and 8B are graphs that schematically illustrate reflected signal intensities measured by opposite beams, in accordance with an embodiment of the present invention.
Figure 8B:
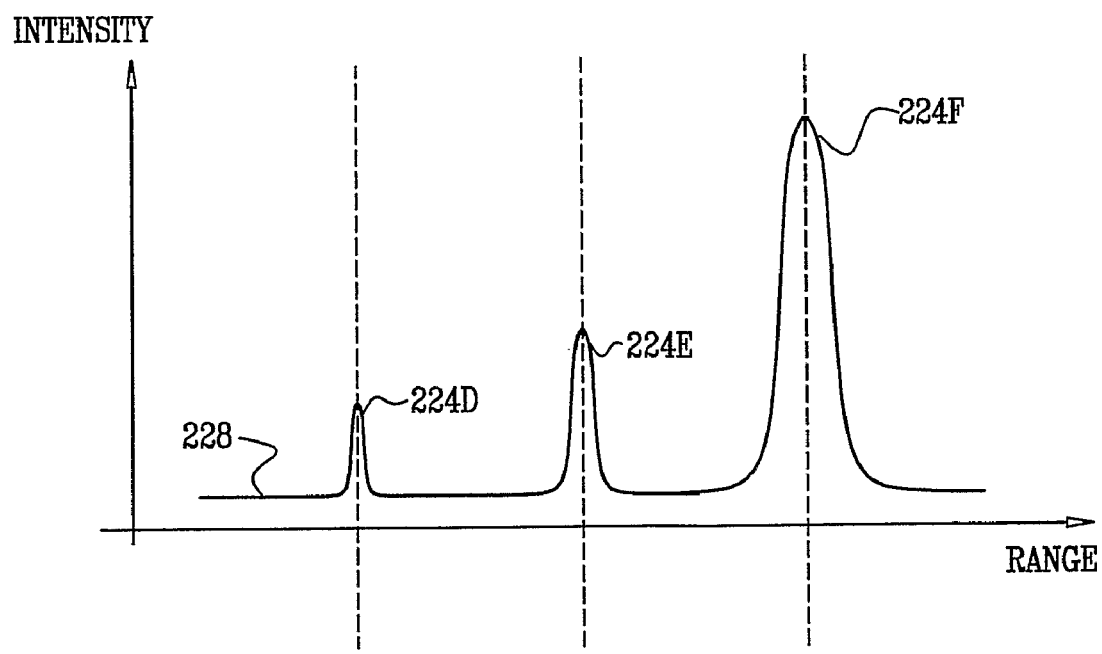

FIGS. 8A and 8B are graphs that schematically illustrate reflected signal intensities measured by opposite beams, in accordance with an embodiment of the present invention. In FIG. 8A, a curve 220 shows the reflection intensity as a function of range, as measured by a particular beam. Curve 220 shows three characteristic peaks 224A, 224B and 224C, which are typically produced by tissue transitions (i.e., interfaces between different tissue types). Peak 224A is a strong peak having the shortest range to the effective antenna. A peak of this kind is usually produced by the body "skin effect," i.e., the transition from free space to tissue when penetrating the skin. Peaks 224B and 224C relate to other transitions from one tissue type to another.

In FIG. 8B, a curve 228 shows the reflection intensity as a function of range, as measured by another beam, which is located at a 180° azimuth offset with respect to the beam of FIG. 8A. In other words, the beam of FIG. 8B images a similar depth cross section of the target organ, but from the opposite direction. Note that the range (horizontal) axis of FIG. 8B is reversed, so as to enable curves 220 and 228 to be compared. Curve 228 also shows three peaks denoted 224D, 224E and 224F. Peaks 224D . . . F correspond to the same tissue transitions as peaks 224A . . . c, respectively, as seen from opposite directions.

In FIGS. 8A and 8B the range coordinates of the peaks in the two opposite beams are shown to coincide with one another. In many practical cases, however, the measured coordinates of the peaks generally differ from one another in the opposite direction measurements because of the differences in local light velocity (local time delay) across the tissue. These differences are used to estimate and compensate for the local tissue time delay.

Figure 9:
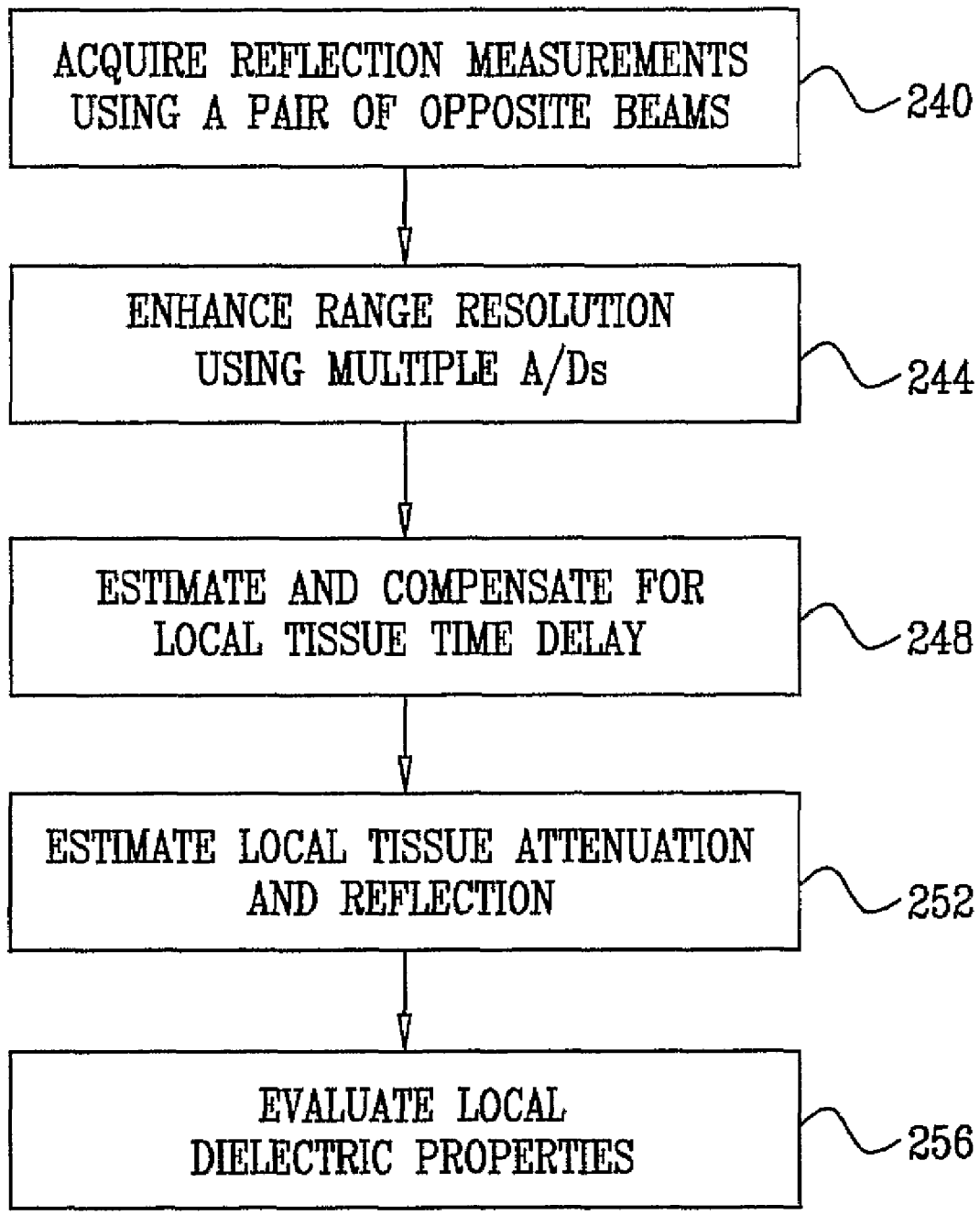
FIG. 9 is a flow chart that schematically illustrates a method for extracting tissue properties from reflected signal intensity measurements, in accordance with an embodiment of the present invention.

FIG. 9 is a flow chart that schematically illustrates a method for extracting tissue properties from reflected signal intensity measurements of opposite beams, in accordance with an embodiment of the present invention. The method of FIG. 9 refers to a particular depth cross section of the target organ, as imaged by a pair of beams at a 180° offset. The process of integrating the data measured by multiple beam pairs at different azimuth angles and heights into a 3-D representation of the target organ is described further below.

The method begins with system 20 acquiring raw reflection measurements using two beams at opposite directions, at a data acquisition step 240. The intensity measurements as a function of range acquired by a particular beam are referred to hereinbelow as a measurement set. The system enhances the range resolution of the two measurement sets by using multiple A/D converters, as described above, at a range resolution enhancement step 244. After reversing the range dimension of one of the measurement sets, the reflection measurements of the two beams resemble the exemplary reflection measurements of FIGS. 8A and 8B above.

In many cases, the skin-effect reflection, i.e., the reflection peak having the shortest range to the effective antenna, is substantially stronger than other, deeper reflections. Temporal side-lobes generated by this peak may distort or mask other reflection peaks. The side-lobes are a result of the point spread function (PSF) of system 20. In some embodiments, the distortion caused by the skin-effect peak can be reduced by detecting the true position of the skin-effect peak, and subtracting from the measured signal a replica of the system PSF, centered at the measured skin-effect peak location. This process is typically performed for each beam position. The skin surface may be added after carrying out the different artifact correction procedures.

System 20 performs time delay estimation and compensation, at a time delay correction step 248. The system identifies in the two measurement sets pairs of characteristic peaks that correspond to the same tissue transition (interface), as viewed from the two opposite directions (such as, for example, the pair 224A and 224D in FIGS. 8A and 8B above). As noted above, the measured peak locations are offset from one another in the two measurement sets due to local time delay differences. For each peak, the system calculates an estimated peak location based on the peak locations in the two measurement sets.

The system then applies piecewise translation and stretching transformations to the horizontal axes of the two measurement sets, which moves the peaks to the estimated locations. Thus, each peak is associated with two time delay offsets, i.e., the time offsets between the original peak location in the two measurement sets and the estimated location. These time offsets are proportional to the cumulative local tissue time delay from the effective antenna and up to the location of the peak. In between peaks, the tissue is assumed to be relatively homogeneous, therefore the time delay offset is distributed uniformly between successive peaks.

For each pair of characteristic peaks, the estimated peak location can be determined as follows: The ranges, measured from the direction of one of the two effective antennas, corresponding to the i'th characteristic peak in the two measurement sets, are denoted $r_i^1$ and $r_i^2$, respectively. The estimated location of the i'th peak is denoted $r_i$. The time delay, with respect to the timing corresponding to the same range in free space, which is caused by the tissue between the (i−1)'th peak and the i'th peak, is denoted $d_i$, when expressed in units of range. Using this notation, it can be shown that:

$$r_i^1 = r_i + \sum_1^i d_i$$

$$r_i^2 = r_i - \sum_{i+1}^P d_i$$

wherein P denotes the number of characteristic pairs of peaks. This set of linear equations can be solved to extract both $r_i$ and $d_i$. These calculations assume there is no time delay outside the subject body.

After completing step 248, the system has an estimate of the local tissue time delay for each point (effective range gate) along the cross section of the target organ.

System 20 estimates the local tissue attenuation, at an attenuation estimation step 252. First, the system calculates the total side-to-side body attenuation along the examined depth cross section. The system identifies in the two measurement sets a pair of peaks that correspond to a particular skin transition (e.g., the pair 224A/224D or the pair 224C/224F in FIGS. 8A and 8B above). The ratio between the reflection intensities of the two peaks is used as an estimate of the total body attenuation.

Using the known total attenuation, the cumulative attenuation from the skin and up to a particular peak can be calculated. The cumulative attenuation is calculated by considering the following four equalities: (1) the total body attenuation is identical in the two measurement sets; (2) the measured peak intensity in the first measurement set (i.e., measured from the direction of the first effective antenna) is equal to the true reflection at the peak location, plus the cumulative tissue attenuation from the skin and up to the peak from this direction; (3) the measured peak intensity in the second measurement set (i.e., measured from the direction of the second effective antenna) is equal to the true reflection at the peak location, plus the cumulative tissue attenuation from the skin and up to the peak from the opposite direction, and (4) the sum of the two cumulative attenuations (from the skin and up to the peak) from the two opposite directions is equal to the known total body attenuation.

The system solves the linear equations derived from these four equalities, and extracts the true reflection coefficient of each peak, as well as the cumulative attenuation between every two successive peaks. The local tissue attenuation and reflection are assumed to be uniform between peaks. Therefore, the cumulative attenuation is distributed uniformly between peaks. The system adjusts the intensity of the measurement sets, so as to compensate for the local attenuation. After completing step 252, the system has estimates of the local tissue attenuation and reflection coefficients for each point (effective range gate) along the cross section of the target organ.

Note that when measuring and manipulating peak intensities, any gain control applied by the receiver should be taken into account. For example, when the receiver employs time-dependent gain control (TGC), the TGC value of each range gate should be taken into consideration, in order to measure the peak intensities correctly.

In some embodiments, the accuracy of the reflection coefficient calculation can be improved by averaging the two attenuation-corrected measurement sets. Additionally or alternatively, the estimation accuracy can be improved by performing several iterations of time delay and attenuation correction. In some embodiments, a background signal per range gate, typically pre-calibrated without the presence of tissue, can be subtracted from the corrected measurement of each range gate. An exemplary pre-calibration process is described further below.

In some embodiments, the estimation process of steps 240-252 above can be performed separately in several spectral sub-bands in order to reduce the effects of signal distortion. For example, the 10 GHz signal bandwidth can be divided into 5-10 sub-bands of 1-2 GHz bandwidth, and the local time delay, reflection and attenuation calculated separately for each sub-band. In order to process each sub-band, the reflected signal should be filtered, so as to retain only the spectral content in the currently-processed sub-band. Such filtering can be performed either before or after the A/D converters, using either analog or digital filtering, respectively. If desired, the corrected measurement sets can be summed over all sub-bands to produce equivalent wideband measurement sets.

The system now uses the three estimated local tissue parameters (local time delay, reflection and attenuation) to evaluate the local dielectric properties along the examined depth cross section, at a dielectric evaluation step 256. Several models are known in the art for calculating dielectric properties based on such physical parameters. For example, a single dielectric layer model is described by Yariv in "Optical Electronics," CBS College Publishing, 1985, Chapter 4, pages 87-95, which is incorporated herein by reference.

The single layer model cited above is particularly suitable for continuous transmission. In some embodiments, a more complex model that considers multiple dielectric layers and pulsed transmission can be used. The model analyzes a structure of multiple adjacent layers having different material composition, with the first layer representing free space. For example, consider a structure of three layers and three transitions (air to first layer, first to second layer, second to third layer). The three layers have dielectric constants denoted $\epsilon_2$, $\epsilon_3$, and $\epsilon_4$. $\epsilon_1 = \epsilon_0$ represents the dielectric constant of air. At the k'th layer transition, the incident wave is denoted $I_k^L$, and the wave progressing to the next layer is denoted $I_k^R$. The incident wave components can be written as $$I_1^L = 1$$
$$I_1^R = |(1+r_1)|$$
$$I_2^L = |(1+r_1)\exp(jk_2\Delta_2)|$$
$$I_2^R = |(1+r_1)\exp(jk_2\Delta_2)(1+r_2)|$$

-continued $$I_3^L = |(1+r_1)\exp(jk_2\Delta_2)(1+r_2)\exp(jk_3\Delta_3)|$$

$$I_3^R = |(1+r_1)\exp(jk_2\Delta_2)(1+r_2)\exp(jk_3\Delta_3)(1+r_3)|$$

wherein $r_i$ denotes the reflection coefficients of the i'th layer transitions, $\Delta_i$ denotes the thickness of the i'th layer, and $k_i$ denotes the wave number in the i'th layer.

At each layer transition there exist reflected (outgoing) wave components from both the present layer transition and from deeper layer transitions. In general, a reflected component originating from the i'th layer transition and having traversed (j−1) layers after being reflected is denoted $O_i^j$. The outgoing components are given by $$O_1^1 = |r_1|$$

$$O_2^1 = |(1+r_1)\exp(jk_2\Delta_2)r_2|$$

$$O_2^2 = |(1+r_1)\exp(jk_2\Delta_2)r_2\exp(jk_2\Delta_2)(1+r_1)|$$

$$O_3^1 = |(1+r_1)\exp(jk_2\Delta_2)(1+r_2)\exp(jk_3\Delta_3)r_3|$$

$$O_3^2 = \left|\begin{array}{c}(1+r_1)\exp(jk_2\Delta_2)(1+r_2)\exp(jk_3\Delta_3)\cdot\\ r_3\exp(jk_3\Delta_3)(1+r_2)\end{array}\right|$$

$$O_3^3 = \left|\begin{array}{c}(1+r_1)\exp(jk_2\Delta_2)(1+r_2)\exp(jk_3\Delta_3)\cdot\\ r_3\exp(jk_3\Delta_3)(1+r_2)\exp(jk_2\Delta_2)(1+r_1)\end{array}\right|$$

The total outgoing signal from the first layer transition is equal to $0_1^1+0_2^2+0_3^3$. $0_n^n$ can be written as $$O_n^n = A \exp(-jwt_n + \phi)\cdot r_n \cdot \left[\prod_{m=2}^{n}\exp(2jk_m\Delta_m)\right]\cdot \left[\prod_{m=1}^{n-1}(1+r_m)^2\right]$$

wherein A denotes the incident signal magnitude, $\phi$ denotes the phase at the first layer transition, $\omega$ denotes the signal angular velocity, and $t_n$ denotes the time index at which the signal was received, corresponding to the two-way path of the beam. Using this model, the dielectric coefficients $\epsilon_i$ can be extracted from the measured results.

The models described above assume a planar incident wave front. In alternative embodiments, the model may be adapted to take into account the spherical decay of spherical wave fronts, such as by dividing the signal by $R^2$. In some cases, the incident wave is not perpendicular to the plane of layer transition, an effect which may also cause the results to be polarization-dependent.

When applying any suitable layer model to the measurements of system 20, the layer thicknesses correspond to distances between successive peaks, after attenuation and time delay correction. Additionally, the local attenuation and reflection coefficients are also known, as described above. The complex permittivity of each layer can be calculated (assuming perpendicular incidence) using the well-known equations $$|r_n| = \left|\frac{\sqrt{\varepsilon_{n+1}}-\sqrt{\varepsilon_n}}{\sqrt{\varepsilon_{n+1}}+\sqrt{\varepsilon_n}}\right|$$

-continued $$|k_n| = \left|k_0\sqrt{\frac{\varepsilon_n}{\varepsilon_0}}\right|$$

wherein $r_n$ and $k_n$ respectively denote the reflection and attenuation of the n'th layer. The imaginary component of the permittivity, denoted $\epsilon''$, and the conductivity, denoted $\sigma$, roughly obey the relationship $\epsilon''=\sigma/\omega$. Therefore, the conductivity $\sigma$ can be derived from the estimated permittivity.

An alternative method for estimating the complex permittivity may be based on the signal within each layer separately. Assuming no losses, the light velocity v in a particular layer is given by:

$$v = \frac{\omega}{k} = \frac{c}{n} = \frac{1}{\sqrt{\mu\varepsilon}}$$

wherein n denotes the index of refraction, and $\omega$ is the signal angular velocity. In the presence of losses, k is complex. Defining k as $$k \equiv \beta - j\frac{\alpha}{2},$$

$\alpha$ and $\beta$ are given by the equations $$\beta^2 - \frac{\alpha^2}{4} = \frac{\omega^2}{c^2}\text{Re}(\varepsilon_r)\quad \beta\alpha = \frac{\omega^2}{c^2}\text{Im}(\varepsilon_r)$$

This model is described in detail by Jackson in "Classical Electrodynamics," John Wiley & Sons Inc., New York, 1999, pages 295-316, which is incorporated herein by reference.

$\alpha$ and $\beta$ may be estimated by measuring the complex signal (before attenuation correction and time-delay compensation) immediately before a reflection peak, and comparing it to the signal at a previous reflection peak. Using the estimated $\alpha$ and $\beta$ values, both the real and imaginary components of the permittivity can be calculated. Note that this model is particularly suitable for narrowband signals, such as when the signal is confined to a particular sub-band of system 20.

Additionally or alternatively, any other suitable model can be used to estimate the dielectric tissue properties based on the measured time delay, reflection and attenuation values.

In summary, the method of FIG. 9 provides estimates of local tissue time delay, reflection and attenuation coefficients, as well as local dielectric properties, based on backscattering intensity measurements made by two beams that irradiate the target organ from opposite directions. Using this method, the reflected signal intensity measurements acquired by the different beams are corrected, to account for local time delay and attenuation.

Most of the parameters measured by system 20 do not typically depend on the geometry of the measurement. For example, Gabriel et al., in "The Dielectric Properties of Biological Tissues: I. Literature Survey," Physics in Medicine and Biology, volume 41, 1996, pages 2231-2249, which is incorporated herein by reference, refer to the dielectric properties of tissue as scalars and not as tensors. Reflection coefficient measurements, on the other hand, often do depend on the geometry of the measurement, e.g., on the angle of incidence with respect to the tissue interface that produces the reflection. In system 20, however, every point in space is measured from multiple directions. As a result, the geometry-dependent effects are inherently averaged and minimized.

The possible spatial dependency of the reflection coefficient, either due to angular dependency of the dielectric properties or due to the effect of the tissue interface geometry, can be used to extract additional clinical information. For example, 3-D reconstructed images may be produced using multiple beam configurations, with the beam configuration changing cyclically from one frame to another. The difference between successive frames may be indicative of the spatial dependency. The beam configurations may differ from one another in several aspects, such as the elevation of the beam with respect to the plane of the cylinder.

Scanning and Reconstruction

System 20 integrates the extracted tissue parameters measured by the different beams, after artifact compensation, into 3-D representations of these parameters. In principle, a scanned volume containing the target organ is divided into horizontal slices, at increments on the order of 1 mm. Each horizontal slice is scanned from multiple directions. Artifacts are compensated for, and parameters are extracted using pairs of opposite beams, as described above. The system then performs two-dimensional (2-D) reconstruction of the reflected signal intensity across the slice, using the data collected by the multiple beams.

Figure 10:
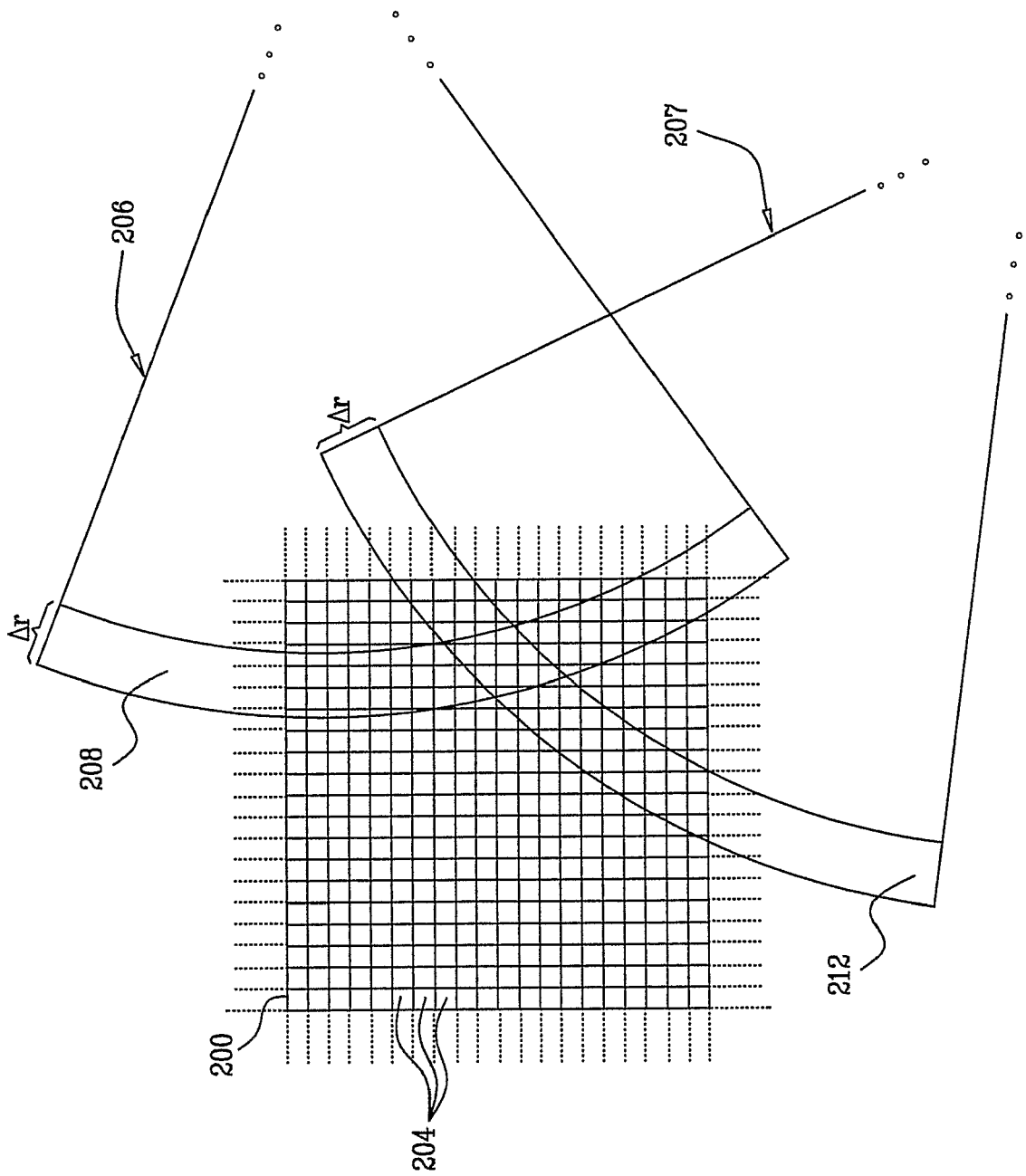
FIG. 10 is a diagram that schematically illustrates two-dimensional signal reconstruction, in accordance with an embodiment of the present invention.

FIG. 10 is a diagram that schematically illustrates two-dimensional signal reconstruction in a particular horizontal slice, in accordance with an embodiment of the present invention. Although the description that follows refers to the 2-D reconstruction of reflected signal intensity values, the method is similarly used for reconstructing the other extracted tissue parameters across the slice. In other words, the method can be used to reconstruct the attenuation, reflection and/or time delay values across the 2-D slice.

The time delay map may be directly translated into a map of local light velocities. The values of the local dielectric properties, as a function of time and space, may be derived from the above three reconstructed images (i.e., the attenuation map, the reflection map and the time delay map).

The diagram shows a top view of a particular slice. The area of the slice is divided by a grid 200 into multiple grid cells 204. Two beams 206 and 207 view the slice from two different directions. The two angular sectors shown in the figure indicate the approximate horizontal beam-widths of the beams.

As described above, for each beam, system 20 measures the reflected signal intensity in 1 mm effective range gates, which are then corrected to account for local time delay and attenuation. In beam 206, a particular effective range gate 208 corresponds to an arc having a width of $\Delta r=1$ mm. A similar effective range gate 212 is shown for beam 207. As can be seen in the figure, each effective range gate covers multiple grid cells 204.

In order to perform 2-D reconstruction of the reflected signal intensity, DSP unit 96 accumulates the intensities contributed to each grid cell 204 by the different beams and effective range gates. For each effective range gate of each beam, the system previously measured a particular intensity value. This intensity value is divided uniformly among the grid cells covered by the effective range gate in question. The process is repeated for all grid cells, beams and effective range gates. At the end of the process, each grid cell has an accumulated value, integrated over the different effective range gates of the different beams scanning the particular slice.

The 2-D reconstruction process described above refers to a particular horizontal slice. The process is repeated for all slices, to produce a 3-D grid. Although the vertical increment between neighboring slices is on the order of 1 mm, the thickness of each slice is derived from the elevation beam-width of the effective antennas used, typically on the order of 15 cm. Thus, there is significant overlap between the slices.

System 20 translates the measurements performed in the overlapping slices into a set of linear equations. Solving the equations achieves a spatial resolution on the order of the increment size (in the present example 1 mm) in the vertical dimension. The equations may be solved, for example, using deconvolution methods. Deconvolution methods are often noise-sensitive. Therefore, a sufficiently high SNR should be obtained.

Accurately solving the equations often involves knowledge of the solution at the boundaries of the scanned region. In some embodiments, protective RF absorbing sheets having a negligible reflection coefficient can be placed at the upper and lower boundaries of the subject's relevant body area, so as to force known boundary conditions. Thus, the equations may be solved analytically.

In some embodiments, the contribution of each effective rage gate can be divided non-uniformly among the grid cells covered by the effective range gate. For example, the distribution can be range-dependent. Alternatively, the distribution can take into account angle-dependent gain differences of the effective antenna. Other known methods, such as iterative back-projection and filtered back-projection, which are sometimes used in tomography systems, can also be used for improving the spatial resolution in system 20.

In the description above, effective range gates are geometrically represented as concentric arcs centered at the phase center of the effective antenna. In many practical cases this representation is inaccurate, since the light velocity in tissue is different from the light velocity in free space, and also between different types of tissue. As a result, the actual geometrical shape of an iso-time surface (i.e., the locus of all points having a certain propagation delay from the effective antenna) deviates from a perfect arc. Estimating the actual shape of the iso-time surfaces produces a more accurate representation of the effective range gates.

For example, the iso-time surfaces can be estimated by considering two different light velocity values, a free space value and a representative light velocity value in tissue. The shape of the iso-time surfaces can be determined based on an estimation of the shape of the patient's outer body surface. Points determined to be within the patient body are assigned the tissue light velocity value, and points determined to be outside the body are assigned the free space value.

The shape of the outer body surface can be estimated, for example, using the following process:

For each beam, measure the minimal distance at which a non-negligible backscattering intensity is received (i.e., measure the minimal distance from the effective antenna phase center to the body surface).

The volume confined within the cylindrical antenna array is represented by a 3-D array, whose values are initially set to zero. For each beam, all the elements whose distance from the effective antenna phase center matches the measured distance to the surface, and that are within the main-lobe of the respective beam, are set to "1". The resulting set of coordinates for each beam typically resembles a dome-shaped surface.

Assume that the point at the 3-D center of the cylinder is located within the scanned tissue. Let us now examine the values of the 3-D array along radial lines originating from the central of the cylinder and pointing to different 3-D angles homogenously spanning the 4π sphere. Along each such radial, the outer surface of the patient body is defined by the 3-D array element whose value is "1" and its distance from the center of the cylinder is minimal.

Additionally or alternatively, the iso-time surfaces can be adjusted according to the local time delay at each point within the patient body. This information is typically available after the reconstruction process (based on outer body surface estimation) is completed. The reconstruction process inherently produces a 3-D map of local time delays in the scanned volume, which can be used to recalculate the iso-time surfaces for each beam. The time delay values can then be used to refine the reconstructed image. Such a procedure may be repeated iteratively, for example until the incremental variations in each iteration become negligible.

In the present example, system 20 scans a volume having a height of 25 cm, a size typical of cardiac imaging. The volume is divided into 250 horizontal slices at 1 mm increments. Each slice is scanned by 360 beams, which are distributed at 1° increments around the perimeter of the cylindrical antenna array. In each beam, two 64-pulse sequences are transmitted. Thus, a total of 250×360×2=180,000 pulse sequences are transmitted in order to scan the volume once. In order to achieve a temporal resolution of 100 Hz, system 20 transmits 18,000,000 pulse sequences per second, yielding the PRI of 1/18,000,000=55 ns shown in FIG. 7 above.

In the present example, the height dimension of the imaged volume is divided into 250 slices using an array having forty antenna elements along the height dimension. When imaging a particular slice, the beams are typically shaped so that their phase centers fall in the plane of the slice. As a result, some of the beams may not be perfectly parallel with the base of the cylinder, i.e., some beams may be slightly tilted in elevation. The tilt is typically on the order of several tenths of a degree, usually no greater than one degree.

In alternative embodiments, other scanning and reconstruction processes can be used. For example, instead of dividing the scanned volume into slices, the vertical dimension can be reconstructed similarly to the horizontal reconstruction method of FIG. 10, since each beam has a certain width in elevation. In general, the volume can be divided into a three-dimensional grid comprising multiple 3-D grid cells. The reflected signal intensity of each 3-D grid cell can be evaluated by scanning over beams in azimuth as well as elevation.

In some cases, some of the beam pairs used in the 2-D reconstruction process contain poor quality data, for example because of poor SNR due to high penetration depth. In these cases, the overlap between the two beams, which view the same depth cross section from opposite directions, may be insufficient for performing artifact compensation. When the overlap region is not sufficient in some beam pairs, 2-D reconstruction of a slice can be carried out in two phases. First, 2-D reconstruction is performed using the beam pairs that have adequate overlap. When the beams of a particular beam pair do not have sufficient overlap, the attenuation and time delay of this beam pair can be corrected using the 2-D reconstructed values of the other beam pairs in the slice. In applications that can tolerate a lower refresh rate, such as non-cardiac applications, the penetration depth (and hence the achievable overlap between opposite beams) can be significantly improved by using longer pulse sequences.

It should be noted that artifacts due to spatial aberrations and multi-path are reduced in system 20, because of the use of relatively wide beams, and because each sample inherently contains information averaged over a large volume. Multi-path artifacts are also reduced due to the relatively strong tissue attenuation involved.

In some embodiments, known super-resolution methods can be used in post-processing to further improve the final spatial resolution of the system. Such methods may comprise, for example, Minimum Variance Methods (MVM), Burg and/or Yule-Walker methods. Super-resolution methods are described, for example, by Borison et al., in "Super-Resolution Methods for Wideband Radar," The Massachusetts Institute of Technology Lincoln Laboratory Journal, (5:3), 1992, pages 441-461, which is incorporated herein by reference. Super-resolution methods may be applied to each beam pair, to each effective slice (i.e., to the data corresponding to a specific height of the cylinder, after 2-D reconstruction), or to the complete 3-D grid.

The 3-D reconstructed tissue parameters are displayed to a user by unit 100 on displays 76 or 83. Different visualization methods and modes can be used. For example, unit 100 can display isometric views of the target organ or parts thereof, with selected tissue parameters shown as color-coded layers on the 3-D display. The display can change dynamically, in accordance with the refresh rate used.

Unit 100 may display selected 2-D slices, projections and other surfaces based of the 3-D information. Real-time 3-D data rendering can be used. Additionally or alternatively, tissue parameters can also be displayed numerically. Typically, the user can control and customize the different display functions using input devices 80. In some embodiments, unit 100 enables the user to perform measurements, such as various length and velocity measurements, based on the 3-D display.

3-D Motion Vector Analysis Mode

In the motion vector analysis mode, system 20 tracks and displays tissue dynamics, such as blood flow. The system produces real-time images showing the 3-D velocity vector of each point in the scanned volume. Tissue velocity is measured using the Doppler effect.

Figure 11:
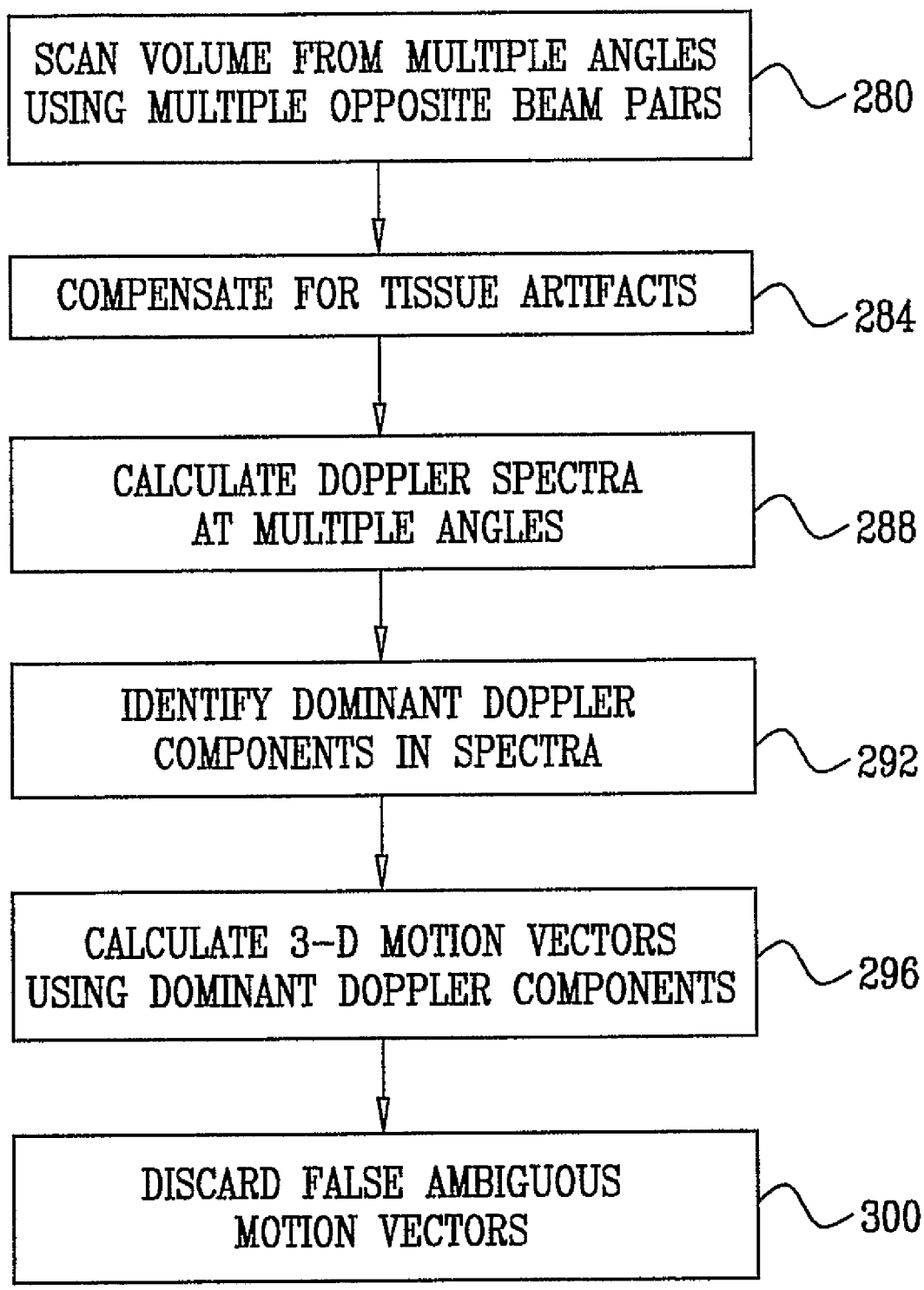
FIG. 11 is a flow chart that schematically illustrates a method for calculating three-dimensional motion vectors, in accordance with an embodiment of the present invention.

FIG. 11 is a flow chart that schematically illustrates a method for calculating three-dimensional motion vectors using Doppler measurements, in accordance with an embodiment of the present invention.

The method begins with system 20 scanning the target organ, at a scanning step 280. The system scans the organ from multiple angles using pairs of opposite beams. In each beam position, several pulse sequences similar to the sequences of FIG. 7 above are transmitted and analyzed. The number of pulse sequences in each beam is on the order of ten, although other values can also be used.

In order to adequately image a relevant range of velocities, the measurements should have a Nyquist frequency of on the order of 3 m/s and a velocity resolution on the order of 0.3 m/s. In order to reach this performance, a refresh rate on the order of 20 Hz is used. In some embodiments, the beams are scanned in an interleaved manner, transmitting a single pulse sequence at a time and returning several times to the same beam position, until the desired number of pulse sequences is transmitted. As a result, the pulse sequences are distributed evenly within the overall scanning cycle. Typically, narrow beams having azimuth and elevation beam widths on the order of 4° are used.

As described below, the Doppler shift measured with respect to a given effective antenna provides information related to a single component of the 3-D tissue velocity vector. In order to reconstruct the 3-D velocity vectors, three or more datasets are acquired. Each dataset provides information for each point in space, from a different viewing angle. The datasets can be acquired, for example, by changing the vertical inclination of the beams from one dataset to another.

For each angular beam position and for each range gate, the measurements are de-convolved to achieve a resolution on the order of 1 mm along the vertical (cylinder height) dimension. The DSP unit then performs artifact compensation on the measurements of each beam pair, at a compensation step 284. The compensation process is similar to the process carried out in steps 248 and 252 of FIG. 9 above.

At the end of this process, at least three sets of measurements are available in cylindrical coordinates, having a spatial resolution on the order of 1 mm. Since there is a significant overlap in azimuth between adjacent beams, de-convolution can also be performed between adjacent horizontal beam angles, per range gate and height slice. De-convolution may also be performed between adjacent height slices, per horizontal beam angle and range gate.

The system calculates the Doppler spectrum of each effective range gate in the scanned volume, as viewed from the direction of each beam, at a spectrum calculation step 288. Using the well-known Doppler equation, the Doppler frequency shift $f_d$ of a particular tissue element can be written as $$f_d = \frac{1}{\lambda}\left(\vec{V}_t \cdot \frac{\vec{R}_s}{|\vec{R}_s|} + \vec{V}_t \cdot \frac{\vec{R}_r}{|\vec{R}_r|}\right)$$

wherein $\lambda$ denotes the signal wavelength, $\vec{R}_s$ denotes the position vector of the tissue element with respect to the transmitting effective antenna, $\vec{R}_r$ denotes the position vector of the tissue element with respect to the receiving effective antenna (which may be the same as the transmitting antenna), and $\vec{V}_t$ denotes the velocity vector of the tissue element. The Doppler spectrum of each tissue element can be calculated, for example, by applying a 16-bin discrete Fourier transform (DFT) to the time-dependent data of each range gate in each beam position. Zero padding may be used to improve the DFT resolution. In some embodiments, a window function may be used to reduce the level of spectral sidelobes.

In some cases, the Doppler shifts measured by a particular effective antenna may have different values with respect to different elements of the effective antenna. This effect may cause some smearing in the Doppler spectrum. The smearing effect can be estimated and compensated for. For example, it may be assumed that the angular Doppler velocity measured by a certain antenna element varies in proportion to $\cos(\theta)$, wherein $\theta$ denotes the angle between the normal to the antenna plane at the phase center of the effective antenna and the normal to the antenna plane at the location of the element in question. Using this assumption, suitable time-and-frequency dependent weighting can be applied to the DFT coefficients.

In some cases, the Doppler spectrum is also smeared as a result of the large signal bandwidth. In order to compensate for this effect, the DFT result can be de-convolved with a point spread function (P SF) that represents the smearing effect. The PSF can be pre-calculated using the Doppler equation, for any given spectral distribution of the transmitted signal.

The system identifies dominant spectral components in the Doppler spectra, at a component identification step 292. Dominant Doppler components typically comprise spectral lines, or frequencies, having relatively strong intensities. Any suitable peak detection method known in the art can be used to determine the peak frequencies. Centroid-based methods can be used to improve the calculation accuracy.

The system attempts to find dominant components that are associated with one another, i.e., relate to the same tissue velocity vector, in different spectra measured from different directions. Using the associated dominant frequencies, the system solves the Doppler equation and calculates the 3-D motion vectors, such as using 3-D triangulation, at a vector calculation step 296.

In many practical cases, however, the Doppler spectra comprise multiple dominant components, and it is sometimes difficult to determine which components in the different spectra are associated with one another. Calculating motion vectors based on Doppler components that are not associated with one another usually produces false, ambiguous motion vectors.

The system detects and discards the false motion vectors, at a discarding step 300. The system may use any suitable method or criterion for detecting false motion vectors. For example, it may be assumed that true motion vectors are continuous in both time and space. In other words, a newly-calculated motion vector should not significantly differ from previously-calculated vectors of the same tissue element, and motion vectors in adjacent tissue elements should not differ significantly from one another. Using these assumptions, motion vectors that vary significantly over time and/or space can be discarded. When using this method, care should be taken at the boundaries of blood vessels, whose velocity is close to zero.

The process described above produces the 3-D motion vectors of different points in the scanned volume. This information can be displayed to the physician either independently or in conjunction with the information of other imaging modes of the system.

As noted above, the beams used in motion vector analysis are relatively narrow. Scanning the target organ with narrow beams may limit the achievable refresh rate. In order to reduce the scanning time, in some embodiments the system transmits with a wide beam and receives with multiple narrow beams simultaneously. The narrow beams point towards the center of the cylinder and have different phase center locations. In order to receive on multiple beams simultaneously, the receiver of the system should comprise multiple parallel receive chains.

The allocation of antenna elements 36 to each receive chain should support data acquisition using opposite beam pairs, in order to perform artifact compensation. For this purpose, in some embodiments the receive beams corresponding to different receive channels are configured to have different phase centers, and the boresight of each receive beam is configured to be perpendicular to the antenna surface at the corresponding phase center.

Figure 12:
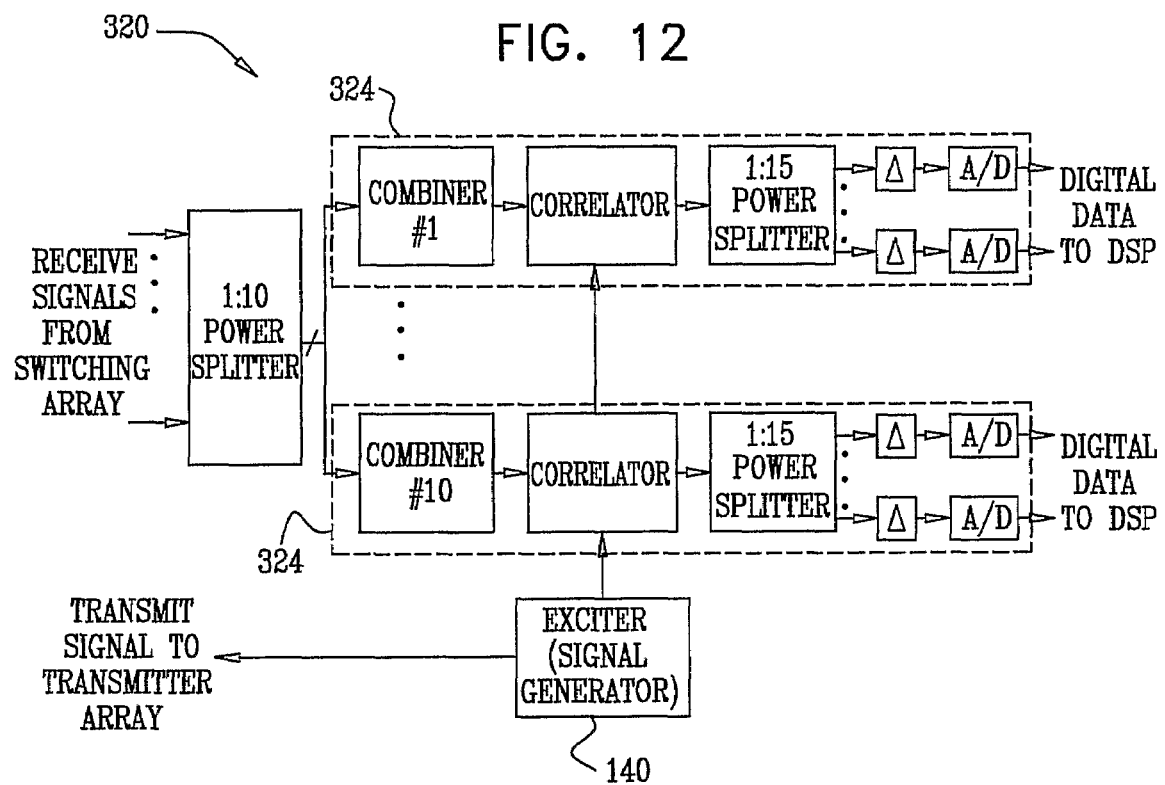
FIG. 12 is a block diagram that schematically illustrates a digital receiver and exciter unit, in accordance with another embodiment of the present invention.

FIG. 12 is a block diagram that schematically illustrates a digital receiver and exciter unit 320, in accordance with another embodiment of the present invention. In unit 320, the received signal is processed simultaneously by multiple receive chains 324. Each receive chain 324 is similar in structure to the receiver of FIG. 5 above. The switching array is configured to provide each receive chain with the signal of the appropriate receive effective antenna.

Since some elements of antenna array 36 are used by multiple effective antennas and multiple receive chains, each of the signals received from switching array 92 is split, e.g., using a 1:10 splitter, and fed to a different combiner in each receive chain 324. Each such combiner, corresponding to a specific receive chain, may use a different apodization scheme, so as to define the required receive beam pattern. In any given receive beam, unused elements 36 are typically given a zero weight.

RF Therapeutic Modes

In the RF therapeutic modes (RF ablation, local heating and electromagnetic pressure modes), system 20 applies concentrated RF energy to a 3-D target region in the target organ. The description that follows refers mainly to RF ablation. Generalization to the other therapeutic modes is straightforward.

Typically, system 20 performs RF ablation interleaved with active imaging of the target region and its vicinity, in order to visualize and guide the ablation process. In some embodiments, the system alternates in time between ablation frames and imaging frames. During the imaging frames, the system performs active 3-D imaging of the target organ, as described above. During the ablation frames, some or all of antenna elements 36 transmit high frequency RF pulses focused on the target ablation region. The 3-D imaging information is used to adaptively track the focal point (i.e., the location of the target region) to which ablation energy is focused.

Adaptive tracking of the ablation region location enables ablation in dynamic organs, such as the cardiac muscle. In order to enable precise tracking, the maximum frame-to-frame motion of the target region should generally not exceed a certain fraction of the ablation resolution. Frame refresh rates on the order of 50 Hz for imaging and 50 Hz for ablation are typically sufficient.

Since imaging and ablation are performed using the same coordinate system, and since the two modes are affected by the same physical artifacts, distortion in the acquired 3-D image typically has little influence on the focal point location accuracy. Additionally, the time delay between each element 36 and the target region, measured in the imaging mode, can be used to optimize the time delay of each transmitting element for ablation, so that pulses from the different elements reach the target region simultaneously.

According to simulated results, the 3 dB width of the ablation region in approximately 0.6 by 0.6 by 3.6 cm, when using a transmission frequency of 18 GHz. Unlike the pulse sequences used for imaging, ablation may be performed using relatively long pulses, so that narrow bandwidths can be used.

In some embodiments, system 20 comprises one or two additional dome-shaped antenna arrays. The combination of the dome-shaped arrays and the cylindrical array approximate a spherical array. In a spherical array, the resolution is substantially uniform in all axes. Such a configuration is expected to provide a spatial ablation resolution of approximately 0.6 cm in all axes.

Additionally or alternatively, system 20 can use directional radiating elements for ablation. The angle between the boresight of each directional element and the normal to the antenna plane at the center of the element can be optimized to maximize the focusing of the ablation beam, with minimal effect on the spatial resolution of the active imaging mode. For example, all directional elements may be oriented so that their boresights point to the center of the cylinder.

The spatial resolution of the ablation mode can also be improved by increasing the frequency of the ablation signal. On the other hand, signal absorption in tissue increases with frequency, so that the transmit power should be increased. It can be shown that the radius of array 32 has little effect on the ablation spatial resolution.

Unlike the other modes of system 20, in which processing may be performed off-line, the processing in the RF ablation mode is performed in real-time. Assuming a volume of 5 cm$^2$, which is imaged with a spatial resolution of 2 mm per axis, the number of slices is reduced from 250 to 25. Each slice comprises 360 beam positions. For each pulse, only six range gates are processed for each A/D converter. In order to obtain a 2 mm resolution, 8 A/D converters should be used, providing 48 samples per pulse, or 96 samples for each pulse sequence (when using two pulse sequences in each transmission). For a frame rate of F frames/second, the number of samples per second is $25 \cdot 360 \cdot 96 \cdot F$, or $8.64 \cdot 10^5 \cdot F$ samples/second. For F=50 frames/second, the acquired data rate is $4.32 \cdot 10^7$ samples/second.

Assuming the data rates given above, a representative digital signal processor (DSP) having a processing power of 15 G floating-point operations per second (Gflop) can perform approximately 330 operations per sample, or 33000 operations per pulse. Higher processing power can be obtained by using multiple signal processors in parallel. Each processor may process a different set of pulses, and the resulting 3-D image matrices can be summed, to produce the final image.

The processing load per pulse sequence is made of three dominant factors:

(1) De-convolution per each effective range gate. There are forty-four effective range gates per pulse sequence, corresponding to a $\sqrt{3} \cdot 5$ cm wide region. In some cases, a $\sqrt{2} \cdot 5$ cm width is also sufficient. A linear combination of eight A/D samples (8 additions and 8 multiplications) is calculated for each pulse sequence. The results of the two pulse sequences are added (i.e., 16 operations×2 pulse sequences, plus one addition, per effective range gate). Thus, a total of approximately 33×44=1452 operations are performed per pulse sequence.

(2) Time delay and attenuation correction: Approximately 500 operations are performed per pulse sequence, i.e., 1000 operations per each pair of opposite beams.

(3) 3-D reconstruction: Each of the twenty-five samples is spread over approximately 25×25 grid cells, producing a total of 15625 operations per pulse sequence.

In total, the overall number of operations per pulse sequence is approximately 20000. For F=50 frames/second, $25 \cdot 360 \cdot 20000 \cdot 50$, or approximately $9 \cdot 10^9$ operations are performed per second.

Once the 3-D image is produced, additional calculations are performed for tissue tracking in order to adaptively track the ablation focal point. Tracking may be carried out by cross-correlating 3-D blocks in successive frames. Alternatively, tracking may be performed by determining the 3-D translation that minimizes the minimum mean-square error (or minimum mean absolute difference) between 3-D blocks in successive frames. For each possible motion vector, $25^3$ multiplications and additions are performed (i.e., a total of 31250 operations). Thus, 1000 possible motion vectors (10 possibilities in each axis) correspond to approximately $31.25 \cdot 10^6$ operations per frame. For F=50 frames/second, approximately $1.6 \cdot 10^9$ operations per second are added.

In summary, a 15 Gflop DSP is typically capable of performing the combined imaging and ablation processing in real-time. Note, however, that if the overlap between opposite beams is insufficient, the processing becomes more complex. In such cases, quicker, lower precision time delay and attenuation correction methods can sometimes be used.

Passive Imaging Mode

Different cell types in the human body, such as nerve and muscle cells, show substantial electrical activity. The propagation velocity within neurons is typically in the range of 30-120 n/s. The duration of action potentials is usually in the range of 1-10 ms, and their amplitude ranges between 70 and 110 mV. The duration of neuron receptor-potentials and synaptic-potentials is typically between 5 and 100 ms, and their amplitude ranges from 0.1 to 10 mV. These properties are described, for example, by Kandel et al., in "Principles of Neural Science," McGraw-Hill, New York, 2000, pages 19-35, which is incorporated herein by reference. The propagation velocities in muscle cells tend to be significantly lower (e.g., it takes about 50 ms for the signal generated by the sinoatrial node in the heart to reach the atrioventricular node).

This electrical activity generates electromagnetic fields. When operating in the passive imaging mode, system 20 senses and maps these fields. The system provides a dynamic 3-D display showing the propagation of electrical signals in a target organ, such as along a nerve or a muscle. The passive and active imaging modes may be combined, so that the system displays the electrical activity overlaid on a 3-D image of the organ produced by active imaging.

Unlike the active imaging mode in which the signal is subject to two-way body attenuation, in passive imaging the signal is only attenuated on its way from the organ to the receiving antenna. Furthermore, the antenna array and receiver front end may be cooled, so that their sensitivity is improved.

In order to detect the relatively weak electromagnetic fields generated by the physiologic electrical activity, the receiver typically integrates over relatively long time intervals. For example, the receiver may use a single A/D converter operating at a sampling rate higher than 1 GHz, typically on the order of 10 GHz, and integrate the data over intervals on the order of 1 μs.

In many practical scenarios, because of the low duty cycle of the sensed electrical activity signals, the receiver will typically sense no more than a single signal within each 1 μsec interval. Narrow receiving beams can be used to further reduce the probability of sensing multiple signals simultaneously.

In some embodiments, system 20 passively senses the electrical activity signals using three or more beams having different orientations. The beams can be received either simultaneously or in alternation. Based on these measurements, the system estimates the 3-D coordinates of the source of the electrical activity, such as using interferometry methods.

Although in some cases using three beams is sufficient, a higher number of beams (e.g., five beams) may be preferable, for example in order to reduce time delay effects caused by light velocity variations in tissue. In some embodiments, different subsets of three beams are used to calculate a single 3-D coordinate estimate. The center of mass of the various estimates is used as an estimate of the signal source coordinate. Alternatively, a local time delay map produced by the active imaging mode may be used to calculate an iso-time surface, which corresponds to the range measured by each beam. The intersection point of the surfaces corresponding to the three (or more) beams should provide a good estimate of the signal source coordinate.

In order to perform the interferometric triangulation calculation, the sensed signal should be processed at a narrow bandwidth. In some embodiments, the sensed signal is filtered using either digital or analog filtering.

Transmit Power Considerations and Experimental Results

The power level that should be used for transmission in system 20 depends primarily on the body attenuation in the relevant imaging scenarios. In the active imaging and motion vector analysis modes, the transmitted power should provide the system with sufficient SNR at the maximum desired penetration depth. On the other hand, the transmitted power should not exceed industry-standard safety recommendations.

In some embodiments, the instantaneous transmitted power of the system (i.e., the instantaneous power summed over the elements of a particular effective antenna) is set to 3 kW in the active imaging and motion vector analysis modes. As will be shown below, this power level is expected to achieve the desired system performance, and also complies with accepted radiation safety limits.

Using the pulse sequences described above, the transmission duty cycle is approximately 11.6%, so that the average power is approximately 350 W. Assuming the body area exposed to the radiation is on the order of 1 m$^2$, the average power per unit body area is 35 mW/cm$^2$. Instruction #6055.11 of the U.S. Department of Defense (DoD) entitled "Protection of DoD Personnel from Exposure to Radiofrequency Radiation and Military Exempt Lasers," Feb. 21, 1995, specifies for exposure durations shorter than 0.1 hours a maximum permissible exposure level of $1/T_{exp}$ mW/cm$^2$ in any interval of $T_{exp}$ hours. For exposure durations longer than 0.1 hours, a maximum of 10 mW/cm$^2$ is permitted. Instruction #6055.11 also states that the restrictions on maximal exposure levels may be relaxed in cases of partial body exposure. Since imaging using the RFIT system only involves several seconds of exposure, the system power level is well within the recommended safety limit.

In order to verify that the specified power level can achieve the desired system performance, the propagation of RF energy in various tissue types was measured using an experimental setup. The objectives of the experiment were (1) to quantify the expected tissue attenuation of different tissue types, and (2) to quantify the difference in tissue attenuation, reflection and time-delay values between the different tissue types.

The experiment was conducted in an anechoic chamber. Short RF pulses in the range 8-18 GHz were generated and analyzed by a time-domain network analyzer connected to a horn antenna. Different tissue samples were irradiated with the RF pulses. Nine lamb tissue samples were tested, namely blood, heart, lungs, bone, liver, kidney, intestine, brain and thigh muscle. Two additional samples containing air and water were also measured.

In each measurement, a particular sample was placed in the anechoic chamber and irradiated with RF pulses from a distance of approximately 65 cm. A double-sided copper-plated PVC sheet was placed behind the irradiated sample in order to reflect the radiation back to the horn antenna and network analyzer. The area of the reflecting sheet approximately matched the size of the sample and the beam-width of the antenna. In some of the measurements, a cascade of two different samples placed one behind the other was tested.

The signal generated by the network analyzer was a stepped-frequency signal, covering the relevant frequency range in 801 pulses of different frequencies. Each pulse was 192 ns wide. The output power used was 1 mW. Different frequency ranges, such as 8-12 GHz, 15-18 GHz and 8-18 GHz, were tested. The network analyzer sampled the signal reflected from the sample and reflecting plate and reconstructed the signal as a function of time. The setup was precalibrated to enable measurement of the net attenuation of the sample.

The network analyzer measurements provided the reflection, attenuation and time delay characteristics of each tissue type. The measured results clearly show that there are significant differences between different tissue types in all three parameters. The absolute attenuation values measured support the feasibility of RFIT system 20 achieving adequate SNR at penetration depths on the order of 30 cm, enabling high-resolution cardiac imaging.

The experiment results were used to verify the transmit power rating of system 20. Since some of the system parameters in the experiment are different from the parameters the RFIT system, the calculation should take these differences into account.

According to the well-known radar equation, $$SNR \propto \frac{P_t G_a^2 G_c G_i}{R^4 L},$$

or, in logarithmic representation, $SNR = P_t + 2G_a + G_c + G_i - 4R - L + C$, wherein SNR denotes the signal to noise ratio of the system, $P_t$ denotes the transmitted power, $G_a$ denotes the antenna one-way gain, $G_c$ denotes the processing gain due to pulse compression, $G_i$ denotes the gain due to integration over multiple pulses, R denotes the range, and L denotes the system and medium (air and tissue) losses.

The following table shows the parameters affecting the achievable SNR both in the experimental setup and in system 20:

| Parameter | Experimental setup [linear] | Experimental setup [dB] | RFIT system [linear] | RFIT system [dB] |
|---|---|---|---|---|
| $P_t$ | $10^{-3}$ W | −30 dBW | $3 \cdot 10^3$ W | 34.8 dBW |
| $G_a$ | 16 | 12 dB | 1508 | 31.8 dB |
| $G_c$ | $1.54 \cdot 10^6$ | 62 dB | 64 | 18 dB |
| $G_i$ | 1 | 0 dB | 2 | 3 dB |
| R | 0.6 m | −2.2 dB-m | 1.7 m | 2.3 dB-m |
| L (medium only) | 32 | 15 dB | X | $X_{dB}$ |
| $A_e$ | N/A | N/A | 0.075 m² | −11.2 dB |

Preserving the SNR of the experimental setup in the RFIT system yields:

$$X_{dB} = \tilde{P}_t + 2\tilde{G}_a + \tilde{G}_c + \tilde{G}_i - 4\tilde{R} - (P_t + 2G_a + G_c + G_i - 4R - L)$$
$$= 34.8 + 63.6 + 18 + 3 - 9.2 - (-30 + 24 + 62 + 0 + 8.8 - 15)$$
$$= 60.4 \text{ dB}$$

wherein the parameters marked ~ denote parameters of the RFIT system and parameters not marked with ~ denote parameters of the experimental setup. Practically, the SNR of the experimental setup is significantly better than the SNR required in system 20, so we may safely assume $X_{db}$=75 dB. Based on the experimental results, such a value corresponds to a penetration depth of approximately 30 cm. This penetration depth is suitable for high penetration depth applications, such as cardiac imaging.

In the RF ablation mode, the transmitted power of system 20 should enable raising the temperature of the target ablation region by approximately 20° C. As described above, the dimensions of the ablation region are approximately 0.6 by 0.6 by 3.6 cm, at the 3 dB points. Assuming the ablation region has the shape of an ellipsoid, its volume is approximately $(4\pi/3) \cdot 0.3 \cdot 0.3 \cdot 1.8 = 0.68$ cm³. Assuming a characteristic tissue density of 1 g/cm³, the mass of the ablation region is approximately 0.7 grams. The energy required to increase the temperature of this mass by 1° C. is 2.9 Joules. Thus, approximately 59 Joules are required for increasing the temperature of the ablation region by 20° C.

Assuming the ablation procedure is 600 second long, the power dissipated in the ablation region should be somewhat greater than 59/600=0.098 W. After reaching the target temperature, the power used is normally decreased, so that the local temperature remains stable (i.e., so that the body heat dissipation mechanism and the RF heating mechanism balance each other).

According to the results of the experiment described above, the maximum one-way power attenuation is approximately 2 dB/cm. This attenuation was measured for blood and water. A pulse traveling a distance of 20 cm in tissue would therefore be attenuated by no more than 40 dB. According to computer simulation results, the ratio between the transmitted power per element and the power at the ablation region is 1:27712 for continuous-wave transmission. Thus, the transmission power per element P should be set to approximately:

$$P = \frac{0.098 \cdot 10000}{27712} W = 35.4 \text{ mW}$$

In the simulated scenario, an array comprising 29964 elements is used, so that the overall RMS power is approximately 1060 W. Assuming the irradiated body area is 1.5 m², the power per unit area is 70 mW/cm², which is well within the short-exposure limits of the DoD safety standard cited above. For longer durations, on the order of 600 seconds (0.1 hours), the power density is acceptable for treatment scenarios.

The calculation above is based on worst-case attenuation assumptions, and in many practical cases the transmitted power can be significantly lower. When system 20 uses additional dome-shaped antenna arrays, the dimensions of the ablation region can be reduced to approximately 0.6 by 0.6 by 0.6 cm. In such configurations, the energy required for ablation is reduced by a factor of six, and the power per unit body area is reduced to approximately 11 mW/cm². In some embodiments, sensitive body parts can be covered by radiation absorbing materials in order to further reduce their exposure. It should be noted that the heating effect decays rapidly outside the 3 dB ablation region. Typically, immediately outside the 3 dB boundary, each tissue point is heated by 0.5° C. or less for each 1° C. temperature increase inside the ablation region.

The experimental setup described above was also used to verify the feasibility of enhancing the range resolution using multiple A/D converters. The reflecting plate and tissue sample were placed at multiple distances from the antenna. The distances were spaced by approximately 1.57 mm from one another, over a 15.7 mm range. The distance offsets are equivalent to the time delay offsets between A/D converters in system 20.

The data measured by the network analyzer was processed in off-line to extract the signal magnitude per each effective range gate. The results clearly showed that the measured signal changed significantly when the sample was moved by increments smaller than the raw range resolution. The measured ranges to the different reflecting surfaces of the sample and plate approximately matched the manually-measured distances.

System Test and Calibration

In some embodiments, different test and calibration procedures may be performed at different life cycle stages of system 20. For example, during installation at a particular site, the installation quality and system integrity are evaluated and corrected if necessary. Attention is typically given to mechanical deformations in array 32, which may affect the relative locations of the various radiating elements. The cable lengths, the accuracy of delay-lines and the attenuation of cables and connectors, which may affect the beam-shaping of the various effective antennas used, are also sometimes tested at installation.

During everyday use of the system, the system may be tested both at the radiating element level and at the effective antenna level. Such tests may be performed periodically or when a fault is detected or suspected.

Radiating element level calibration and test may be performed using an accurately-manufactured calibration sphere, which is positioned at the center of the cylindrical antenna array. For each element 36, pulses are transmitted and received using the element. Receiving a signal whose power is within an expected range is indicative of the integrity of the entire transmit-receive chain. The power of the received signal may also be used for compensating for the attenuation along the two-way path from the exciter to the element. Furthermore, the minimal range at which a non-negligible reflection is detected, corresponding to the distance to the sphere surface, can be used for minimizing range bias. Other calibration procedures may involve transmitting pulses from a particular element 36, and receiving the signal at several adjacent elements. The relative timing of the reflections can be used for minimizing phase misalignment between adjacent elements.

At the effective antenna level, a specially-manufactured phantom (i.e., an artificial body imitating an imaged object) can be placed at pre-determined locations within the cylindrical array. Pulses are transmitted from each possible effective antenna. The reflection from the phantom is received by the effective antenna, as a function of range. Separate measurements can be performed for each frequency sub-band. The minimal range at which a non-negligible reflection is detected can be used for range calibration. Significant deviations from the expected signal may indicate failure or performance degradation.

In some embodiments, as described above, the background signal (i.e., the signal output by the receiver without the presence of a reflecting object) is subtracted from the output of each received beam during image reconstruction. The background signal is typically pre-measured for each possible effective antenna. The background signal of each effective antenna is often measured as a function of range and for each frequency sub-band.

Data Acquisition Load Estimation

As noted above, measured data can be collected in system 20 either in real-time or off line (with the exception of RF therapeutic mode, in which data is typically collected on-line). When operating off-line, the acquired data is stored in DSP unit 96 or in data processor unit 100. Typically, the duration of a complete off-line data acquisition cycle is on the order of 1 second.

In the active imaging mode, fifteen A/D converters sample the signal simultaneously. Assuming a 10 GHz signal bandwidth, a range gate of 1.5 cm and a region of interest that is 50 cm deep, the number of samples per pulse per A/D converter is 35. When using B bits per sample (e.g., B=20 bits, 10 bits per complex component), the number of bits per pulse per A/D converter is 35·B. For 15 simultaneous A/D converters, the number of bits per pulse is 525·B. For a pulse repetition frequency (PRF) of 18 MHz, the data acquisition rate is 9.45·B Gbit/sec.

In the motion vector analysis mode, in comparison to the active imaging mode, datasets are collected from three different directions, at a lower refresh rate (typically one fifth of the refresh rate used for active imaging). Multiple pulse sequences, typically 10 sequences, are used per beam position. The data acquisition rate is thus 3·10/5=6 times higher than the data rate of the active imaging mode, or 56.7·B Gbit/sec.

In the RF therapeutic modes, data acquisition is performed for real-time imaging and guidance. The frame rate used is typically half the rate used in active imaging, and the number of vertical slices used is typically one tenth of the number of slices used in active imaging. Moreover, a smaller region of only 5 cm$^3$ region is typically imaged. The number of samples per pulse is approximately 3.8 times lower than in active imaging, yielding a data acquisition rate of approximately 125·B Mbit/sec.

In the passive imaging mode data is collected at a very high rate, typically on the order of 10 GHz. Data is collected from M beams simultaneously. Each sample uses B bits. The resulting data acquisition rate is 10·M·B Gbit/sec.

Although the embodiments described herein mainly address cardiac applications, the methods and systems described herein can also be used for imaging and applying treatment to any other organ or system. RFIT methods and systems can be used for detecting and removing tumors, such as in the different fields of oncology. The tissue classification capability can be used for tissue analysis in pathology. Measuring local conductivity can be used in different neurological applications. Other applications may include veterinary applications and general clinical research.

Variations of the RFIT system can be used as all-in-one diagnosis and/or treatment tools in environments having limited access to hospitals, such as remote rural areas, oil barges, ships and space stations.

RFIT systems can apply additional types of treatment. For example, assuming plaque or other material deposited in arteries is particularly sensitive to heat in comparison with the surrounding tissue, a low power RFIT system can use RF ablation to treat arterial stenosis, such as in the coronary arteries. RF ablation can also be used to destroy emboli. An additional application of the local heating mode may be the activation of temperature-activated drugs. Such drugs can be introduced into the patient body and activated only in a particular location or organ by applying local heating.

Other applications of RFIT methods and systems may be in orthopedics and sports medicine. For example, the capability to perform 3-D imaging at extremely high refresh rates enables gathering kinetic data regarding skeletal motion and the motion of muscles.

The different RFIT modes, and in particular the local heating mode, can be used in different para-medical applications. For example, local heating can be used in cosmetics, such as for treating different dermatological conditions. Applications may also exist in alternative medicine.

RFIT methods and systems can also be used in non-medical applications. For example, an RFIT system can be used for 3-D modeling of temperature-sensitive materials and 3-D imaging of non-metallic objects in various industrial applications.

RFIT methods and systems can also be used for security applications. For example, the ability to measure conductivity with high spatial resolution can be used to remotely detect concealed weapons. A variation of the local heating mode can be used to temporarily incapacitate a person identified as carrying a concealed weapon. The tissue characterization capability of the system can be used to detect explosives, drugs and other illegal substances.

The RFIT systems described hereinabove are based on backscattering reflections. An alternative high resolution imaging system may also be based on attenuation. The attenuation-based system can use a cylindrical array of radiating elements, which transmits relatively wide beams, approximately corresponding to the width of the imaged organ. The attenuated signal is received by multiple narrow beams concurrently. The receive beams may either span several locations in azimuth, or several locations in both azimuth and elevation. Both transmit and receive beams should point to the long axis of the subject, but receive and transmit beams should be located at different sides of the subject. The transmit beams may span 180° or 360° around the circumference of the cylinder.

In principle, an attenuation-based system can provide a two-dimensional or one-dimensional array of attenuation parameters for each transmit beam position. Improved performance may be obtained by transmitting at several elevations along the cylinder height. Image reconstruction can use known methods, such as reconstruction methods used in computerized tomography (CT) imaging systems.

In order to reduce the effects of refraction, which cause the beams to deviate from a straight line, each receive beam may be relatively wide. In such cases, adjacent receive beams should have an overlapping mainlobe, and the angular resolution can be achieved by de-convolution procedures.

Attenuation-based systems can use narrowband RF signals, so as to simplify the hardware used. In addition, the power used should only assume one-way attenuation, so that high penetration depths may be achieved. In some embodiments, the attenuation-based system can use mechanical antenna scanning. A wide-angle source (e.g., a horn antenna) may be placed on one side of the subject, and an array of multiple receive beams (e.g., an antenna with digital beam-forming or an array of discrete antennas) can be placed on the opposite side. The two antennas are mechanically-scanned around the subject in one or two dimensions. In applications in which a high refresh rate is not mandatory, a single-beam receiving antenna may be used, and the multiple receive beams can be generated by transmitting a series of pulses for each beam position, and moving the receive antenna from pulse to pulse.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for imaging, comprising:
    directing a plurality of radio frequency (RF) beams toward a target organ from a respective plurality of angles, the plurality of the RF beams comprising one or more first pairs of the RF beams, each first pair comprising two of the RF beams that impinge on the target organ from opposite directions;
    receiving RF signals reflected from the target organ responsively to the RF beams, the RF signals comprising one or more second pairs of the RF signals engendered respectively by the one or more first pairs of the RF beams using a processor to perform the following steps;
    extracting local tissue parameters at multiple points in the target organ by jointly processing the RF signals in each of the second pairs; and
    producing images of the target organ using the extracted local tissue parameters.

2. The method according to claim 1, wherein directing the plurality of the RF beams comprises forming a respective plurality of effective antennas directed to the target organ from the plurality of the angles by selectively activating subsets of radiating elements selected from an antenna array comprising a plurality of the radiating elements.

3. The method according to claim 1, wherein directing the plurality of the RF beams comprises at least one of:
    mechanically scanning one or more antennas so as to transmit from the plurality of the angles; and
    mechanically scanning the target organ with respect to one or more antennas so as to cause the RF beams generated by the antennas to impinge on the target organ from the plurality of the angles.

4. The method according to claim 1, wherein directing the plurality of the RF beams comprises transmitting one or more wideband RF pulses in each of the RF beams.

5. The method according to claim 4, wherein transmitting the one or more pulses comprises transmitting a sequence of two or more wideband RF pulses and phase-encoding the sequence by assigning respective phases to the pulses depending on positions of the pulses in the sequence.

6. The method according to claim 1, wherein receiving the RF signals comprises sampling the reflected RF signals using multiple analog-to-digital (A/D) converters having incremental time offsets with respect to one another, and enhancing a range resolution of the reflected RF signals using multiple outputs of the multiple analog-to-digital (A/D) converters.

7. The method according to claim 1, wherein the local tissue parameters comprise at least one parameter selected from a group of parameters consisting of a local attenuation coefficient, a local reflection coefficient, a local time delay and a local tissue dielectric property.

8. The method according to claim 1, wherein receiving the RF signals comprises measuring for each of the second pairs first and second reflection intensity profiles indicating intensities of the RF signals in the each of the second pairs as a function of time;

wherein jointly processing the RF signals comprises comparing the first and second reflection intensity profiles; and wherein comparing the first and second reflection intensity profiles comprises identifying in the first reflection intensity profile first reflection peaks reflected from respective tissue interfaces in a first direction, identifying in the second reflection intensity profile second reflection peaks reflected from the respective tissue interfaces in a second direction opposite to the first direction, and calculating corrected values of the local tissue parameters responsively to differences between the first and second reflection peaks.

9. The method according to claim 8, wherein calculating the local tissue parameters comprises correcting at least one artifact selected from a group consisting of a local time delay and a local attenuation in the first and second reflection intensity profiles;

wherein producing the images of the target organ comprises reconstructing a three-dimensional (3-D) representation of the local tissue parameters by calculating accumulated contributions of the corrected values of the local tissue parameters of the second pairs at the multiple points in the target organ;

wherein at least some of the RF beams overlap one another, and wherein reconstructing the 3-D representation comprises improving a spatial resolution of the 3-D representation using the overlapping RF beams; and wherein calculating the accumulated contributions comprises calculating, for each beam, iso-time surfaces defining loci of some of the multiple points in the target organ having a particular propagation delay with respect to an antenna directing the beam.

10. The method according to claim 1, wherein directing the RF beams, receiving the RF signals and extracting the tissue parameters comprise continually scanning the target organ using the RF beams, and wherein producing the images of the target organ comprises producing a sequence of 3-D images that display a variation of the extracted tissue parameters over time.

11. The method according to claim 10, and comprising tracking a temporal variation of a tissue region by measuring differences among respective locations of the tissue region in the sequence of 3-D images.

12. The method according to claim 1, wherein producing the images of the target organ comprises at least one of:
differentiating between first and second different tissue types using the extracted local tissue parameters;
identifying a tissue type using the extracted local tissue parameters; and
measuring a local conductivity in at least some of the multiple points in the target organ using the extracted local tissue parameters.

13. The method according to claim 1, wherein directing the RF beams comprises configuring a first subset of the RF beams to use a first polarization and a second subset of the RF beams to use a second polarization different from the first polarization, and wherein extracting the local tissue parameters comprises calculating first values of the local tissue parameters responsively to the first subset of the beams and second values of the local tissue parameters responsively to the second subset of the beams.

14. The method according to claim 1, wherein receiving the RF signals comprises filtering the received RF signals to produce first and second partial bandwidth RF signals, and wherein extracting the local tissue parameters comprises calculating first values of the local tissue parameters responsively to the first partial bandwidth RF signal and second values of the local tissue parameters responsively to the second partial bandwidth RF signal.

15. The method according to claim 1, and comprising inserting a contrast agent affecting at least one of the local tissue parameters into the target organ.

16. The method according to claim 1, and comprising applying RF ablation to an ablation region in the target organ by focusing an ablating signal on the ablation region using at least some of the RF beams, wherein focusing the ablating signal on the ablation region comprises directing the ablating signal based on the produced images of the target organ.

17. The method according to claim 1, and comprising at least one of:
locally heating a region of the target organ by focusing a heating RF signal on the region using at least some of the RF beams; and
applying an electromagnetic pressure to a region of the target organ by focusing an RF signal on the region using at least some of the RF beams.

18. An imaging system, comprising:
one or more antennas, which are arranged to direct a plurality of radio frequency (RF) beams toward a target organ from a respective plurality of angles, the plurality of the RF beams comprising one or more first pairs of the RF beams, each first pair comprising two of the RF beams that impinge on the target organ from opposite directions;
a receiver, which is arranged to receive via the one or more antennas RF signals reflected from the target organ responsively to the RF beams, the RF signals comprising one or more second pairs of the RF signals engendered respectively by the one or more first pairs of the RF beams; and
a processor, which is arranged to extract local tissue parameters at multiple points in the target organ by jointly processing the RF signals in each of the second pairs and to produce images of the target organ using the extracted local tissue parameters.

19. The system according to claim 18, wherein the one or more antennas comprise an antenna array comprising a plurality of radiating elements, and comprising a switching array, which is controlled by the processor and arranged to form a plurality of effective antennas directed to the target organ from the plurality of the angles by selectively activating subsets of the radiating elements.

20. The system according to claim 19, wherein the antenna array comprises a cylindrical array surrounding the target organ, and wherein the RF beams are parallel, with an offset no greater than one degree, to a base of the cylinder and point toward a central axis of the cylinder from multiple azimuth angles and heights.

21. The system according to claim 18, and comprising means for at least one of:
arranging the one or more antennas to mechanically scan the target organ so as to transmit from the plurality of the angles; and
mechanically scanning the target organ with respect to one or more antennas so as to cause the RF beams generated by the antennas to impinge on the target organ from the plurality of the angles.

22. The system according to claim 18, and comprising a transmitter, which is arranged to drive the antennas with one or more wideband RF pulses.

23. The system according to claim 18, wherein the receiver comprises multiple analog-to-digital (A/D) converters, which are arranged to sample the reflected RF signals at incremental time offsets with respect to one another; and wherein the processor is arranged to enhance a range resolution of the reflected RF signals using multiple outputs of the multiple analog-to-digital (A/D) converters.

24. The system according to claim 18, wherein the processor is arranged to carry out at least one of:

measure for each of the second pairs first and second reflection intensity profiles indicating intensities of the RF signals in the each of the second pairs as a function of time, and to extract the local tissue parameters by comparing the first and second reflection intensity profiles;

identify in the first reflection intensity profile first reflection peaks reflected from respective tissue interfaces in a first direction, to identify in the second reflection intensity profile second reflection peaks reflected from the respective tissue interfaces in a second direction opposite to the first direction, and to calculate corrected values of the local tissue parameters responsively to differences between the first and second reflection peaks;

correct at least one artifact selected from a group consisting of a local time delay and a local attenuation in the first and second reflection intensity profiles;

reconstruct a three-dimensional (3-D) representation of the local tissue parameters by calculating accumulated contributions of the corrected values of the local tissue parameters of the second pairs at the multiple points in the target organ;

track a temporal variation of a tissue region by measuring differences among respective locations of the tissue region in the sequence of 3-D images;

differentiate between first and second different tissue types using the extracted local tissue parameters;

identify a tissue type using the extracted local tissue parameters; and measure a local conductivity in at least some of the multiple points in the target organ using the extracted local tissue parameters.

25. The system according to claim 18, wherein said one or more antennas and said processor are arranged to apply RF ablation to an ablation region in the target organ, by focusing an ablation signal on said ablation region using at least some of the RF beams; and wherein said processor is arranged to control the one or more antennas to direct the ablation signal according to a produced image of the target organ.

* * * * *